US010682043B2

(12) United States Patent
Matsumoto

(10) Patent No.: US 10,682,043 B2
(45) Date of Patent: Jun. 16, 2020

(54) MEASUREMENT PROBE AND BIO-OPTICAL MEASUREMENT SYSTEM WITH CONTACT DETECTION

(71) Applicant: OLYMPUS CORPORATION, Hachioji-shi, Tokyo (JP)

(72) Inventor: Koji Matsumoto, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 471 days.

(21) Appl. No.: 15/499,512

(22) Filed: Apr. 27, 2017

(65) Prior Publication Data

US 2017/0224221 A1 Aug. 10, 2017

Related U.S. Application Data

(63) Continuation of application No. PCT/JP2015/066686, filed on Jun. 10, 2015.
(Continued)

(51) Int. Cl.
*A61B 1/07* (2006.01)
*A61B 1/002* (2006.01)
(Continued)

(52) U.S. Cl.
CPC .......... *A61B 1/00167* (2013.01); *A61B 1/002* (2013.01); *A61B 1/07* (2013.01);
(Continued)

(58) Field of Classification Search
CPC ..... A61B 5/0075; A61B 1/002; A61B 1/0684; A61B 5/6885; A61B 1/07; A61B 5/0084;
(Continued)

(56) References Cited

U.S. PATENT DOCUMENTS 7,652,772 B2 1/2010 Backman et al.
2007/0129615 A1 6/2007 Backman et al.
(Continued)

FOREIGN PATENT DOCUMENTS

JP H05-103773 A 4/1993
JP 2004-177257 A 6/2004
(Continued)

OTHER PUBLICATIONS

Sep. 1, 2015 Search Report issued in International Patent Application No. PCT/JP2015/066686.

*Primary Examiner* — Theodore J Stigell
*Assistant Examiner* — Johnathan Maynard
(74) *Attorney, Agent, or Firm* — Oliff PLC

(57) ABSTRACT

A measurement probe is configured to be detachably connected to a bio-optical measurement apparatus and includes: an illuminating fiber configured to irradiate body tissues with illumination light; light receiving fibers configured to receive return light of the illumination light reflected and/or scattered from the body tissues; an optical element configured to transmit the illumination light and the return light and to keep distances between the body tissues and distal ends of the illuminating fiber and the light receiving fibers, constant; and a contact detecting fiber configured to receive the return light to detect contact between a distal end face of the optical element and the body tissues, and detect the return light at a detection region on the distal end face through which the illumination light and the return light pass. The detection region is located outside an illumination region of the illuminating fiber.

11 Claims, 26 Drawing Sheets

Related U.S. Application Data

(60) Provisional application No. 62/091,154, filed on Dec. 12, 2014.

(51) Int. Cl.
    *A61B 1/00*      (2006.01)
    *A61B 5/00*      (2006.01)

(52) U.S. Cl.
    CPC .......... *A61B 5/0075* (2013.01); *A61B 5/0084* (2013.01); *A61B 1/00096* (2013.01); *A61B 1/00105* (2013.01); *A61B 5/6885* (2013.01)

(58) Field of Classification Search
    CPC ............ A61B 1/00105; A61B 1/00096; A61B 1/00167
    See application file for complete search history.

(56) References Cited

U.S. PATENT DOCUMENTS

| | | | |
|---|---|---|---|
| 2008/0037024 A1* | 2/2008 | Backman | G01J 3/02 356/446 |
| 2009/0137893 A1* | 5/2009 | Seibel | A61B 1/0005 600/407 |
| 2013/0211262 A1* | 8/2013 | Suga | G01N 21/474 600/478 |
| 2013/0235384 A1* | 9/2013 | Shono | A61B 5/0075 356/479 |
| 2014/0185036 A1* | 7/2014 | Ito | A61B 1/00057 356/73 |
| 2014/0192362 A1* | 7/2014 | Takaoka | A61B 1/042 356/448 |
| 2015/0038955 A1* | 2/2015 | Bragagna | A61B 5/6843 606/12 |
| 2015/0164333 A1 | 6/2015 | Ito et al. | |
| 2015/0190056 A1 | 7/2015 | Kamimura | |

FOREIGN PATENT DOCUMENTS

| | | |
|---|---|---|
| JP | 2005-40400 A | 2/2005 |
| JP | 2009-537014 A | 10/2009 |
| JP | 2009-537285 A | 10/2009 |
| JP | 2013-244313 A | 12/2013 |
| WO | 2007133684 A2 | 11/2007 |
| WO | 2012147585 A1 | 11/2012 |
| WO | 2014042156 A1 | 3/2014 |

* cited by examiner

MEASUREMENT PROBE AND BIO-OPTICAL MEASUREMENT SYSTEM WITH CONTACT DETECTION

CROSS-REFERENCE TO RELATED APPLICATIONS

This application is a continuation of PCT international application Ser. No. PCT/JP2015/066686 filed on Jun. 10, 2015 which designates the United States, incorporated herein by reference, and which claims the benefit of priority from U.S. provisional application No. 62/091,154 filed on Dec. 12, 2014, incorporated herein by reference.

BACKGROUND

1. Technical Field

The disclosure relates to a measurement probe detachably connected to a bio-optical measurement apparatus for measuring optical characteristics of body tissues. The disclosure also relates to a bio-optical measurement system.

2. Related Art

Conventionally, a bio-optical measurement system has been known which irradiates the body tissues with illumination light and estimates characteristics (property) of the body tissues based on a measured value of return light reflected or scattered from the body tissues. The bio-optical measurement system includes an optical measurement apparatus having a light source for irradiating the body tissues with the illumination light and a detection unit for detecting the return light from a measuring target and a measurement probe detachably connected to the optical measurement apparatus and for irradiating the body tissues with irradiation light and receiving the return light from the body tissues.

The measurement probe includes a fiber unit having an illuminating fiber and a light receiving fiber. The illuminating fiber is connected to the light source at one end thereof and is configured to irradiate the body tissues with the illumination light from the other end thereof. The light receiving fiber is connected to the detection unit at one end thereof and is configured to receive, at the other end thereof, return light from the body tissues irradiated by the illuminating fiber.

In the bio-optical measurement system, low-coherence enhanced backscattering (LEBS) is used in which the characteristics of the body tissues is detected by irradiating the body tissues with white low-coherent light having a short space coherence length from the distal end of the illuminating fiber of the measurement probe and measuring an intensity distribution of the scattered light of a plurality of angles by using a plurality of light receiving fibers (refer to WO 2007/133684).

Here, in the above-mentioned LEBS, the characteristics of the body tissues is detected in a state where the distal end face of the measurement probe is brought into contact with the body tissues (contact object). Therefore, a technique in which the distal end face of the measurement probe is surely brought into contact with the body tissues has been required.

A measurement probe is disclosed in which the distal end can be strongly pushed to the body tissues by providing a bellows-shaped elastic member at the distal end of the measurement probe as a member for surely bringing the distal end face of the measurement probe into contact with the body tissues (refer to JP 05-103773 A).

SUMMARY

In some embodiments, provided is a measurement probe configured to be detachably connected to a bio-optical measurement apparatus for performing optical measurement on body tissues. The measurement probe includes: an illuminating fiber configured to irradiate the body tissues with illumination light; a plurality of light receiving fibers configured to receive return light of at least one of the illumination light reflected and scattered from the body tissues and the illumination light reflected or scattered from the body tissues; an optical element configured to transmit the illumination light and the return light and to keep distances between the body tissues and distal ends of the illuminating fiber and the plurality of light receiving fibers, constant; and a contact detecting fiber configured to receive the return light to detect contact between a distal end face of the optical element and the body tissues, and configured to detect the return light at a detection region on the distal end face through which the illumination light and the return light pass, the detection region being located outside an illumination region of the illuminating fiber.

In some embodiments, a bio-optical measurement system includes a bio-optical measurement apparatus configured to perform optical measurement on body tissues, and a measurement probe configured to be detachably connected to the bio-optical measurement apparatus. The measurement probe includes: an illuminating fiber configured to irradiate the body tissues with illumination light; a plurality of light receiving fibers configured to receive return light of at least one of the illumination light reflected and scattered from the body tissues and the illumination light reflected or scattered from the body tissues; an optical element configured to transmit the illumination light and the return light and to keep distances between the body tissues and distal ends of the illuminating fiber and the plurality of light receiving fibers, constant; and a contact detecting fiber configured to receive the return light to detect contact between a distal end face of the optical element and the body tissues, and configured to detect the return light at a detection region on the distal end face through which the illumination light and the return light pass, the detection region being located outside an illumination region of the illuminating fiber. The bio-optical measurement apparatus includes: a detection unit configured to detect an intensity of the return light received by the contact detecting fiber; and a determination unit configured to determine that the distal end face has contacted the body tissues if decrease in the intensity of the return light detected by the detection unit is equal to or more than a predetermined threshold.

The above and other features, advantages and technical and industrial significance of this invention will be better understood by reading the following detailed description of presently preferred embodiments of the invention, when considered in connection with the accompanying drawings.

DETAILED DESCRIPTION

Exemplary embodiments of the measurement probe and the bio-optical measurement system according to the present invention will be described in detail below with reference to the drawings. The same reference signs are used to designate the same elements throughout the drawings. The drawings are schematic, and relationship between thickness and width of each member, a ratio of each member, and the like are different from those in reality. Also, a figure includes a part having the relationship of dimensions and ratio different from those of other figures. The present invention is not limited to the embodiments.

First Embodiment

Configuration of Bio-Optical Measurement System

Figure 1:
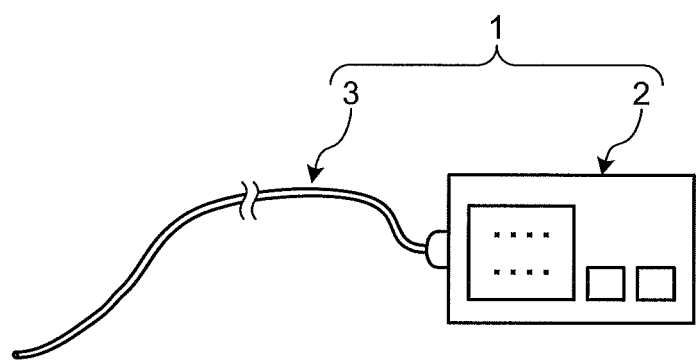
FIG. 1 is a schematic diagram of a configuration of a bio-optical measurement system according to a first embodiment of the present invention.
Figure 2:
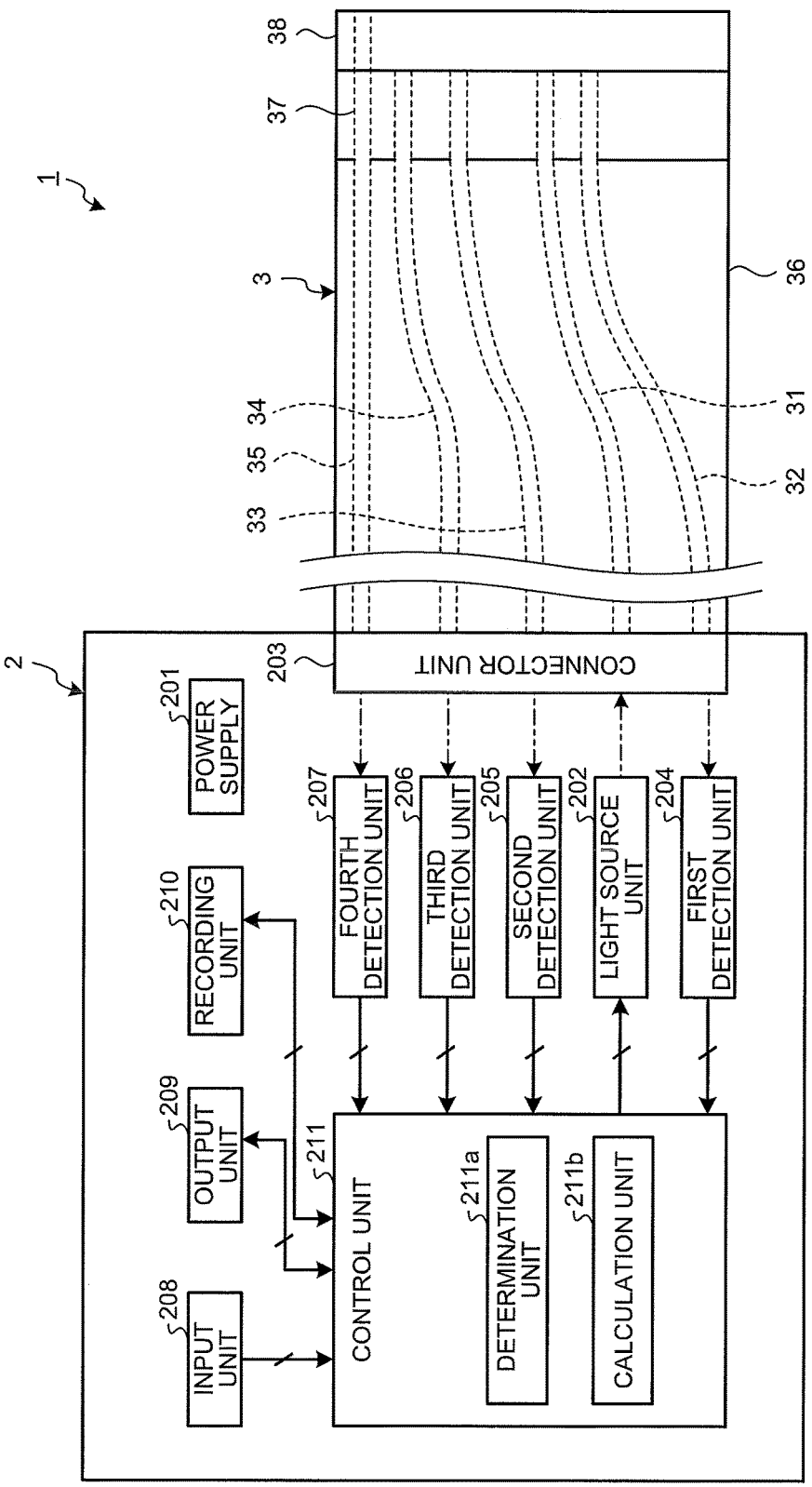
FIG. 2 is a schematic block diagram of the configuration of the bio-optical measurement system according to the first embodiment of the present invention.

FIG. 1 is a schematic diagram of a configuration of a bio-optical measurement system according to a first embodiment of the present invention. FIG. 2 is a schematic block diagram of the configuration of the bio-optical measurement system according to the first embodiment of the present invention.

A bio-optical measurement system 1 illustrated in FIGS. 1 and 2 includes a bio-optical measurement apparatus 2 for detecting characteristics (property) of a measuring target by performing optical measurement on the measuring target such as body tissues which are scatterers and a measurement probe 3 detachably connected to the bio-optical measurement apparatus 2. A side of a distal end of the measurement probe 3 is inserted into a subject.

Configuration of Bio-Optical Measurement Apparatus

First, a configuration of the bio-optical measurement apparatus 2 will be described. The bio-optical measurement apparatus 2 illustrated in FIGS. 1 and 2 includes a power supply 201, a light source unit 202, a connector unit 203, a first detection unit 204, a second detection unit 205, a third detection unit 206, a fourth detection unit 207, an input unit 208, an output unit 209, a recording unit 210, and a control unit 211. The power supply 201 supplies power input from outside to each element of the bio-optical measurement apparatus 2.

The light source unit 202 irradiates the measuring target such as the body tissues with illumination light via the connector unit 203 and the measurement probe 3. The light source unit 202 is configured of an incoherent light source such as a white light emitting diode (LED), a xenon lamp, a tungsten lamp, and a halogen lamp and a coherent light source such as a laser. The light source unit 202 is formed by combining it with an optical lens so that a light guiding efficiency to an optical fiber in the measurement probe 3 can be improved.

The measurement probe 3 is detachably connected to the connector unit 203. The connector unit 203 propagates the illumination light irradiated by the light source unit 202 to the measurement probe 3 and propagates a plurality of light beams entered from the measurement probe 3 to the first detection unit 204, the second detection unit 205, the third detection unit 206, and the fourth detection unit 207.

The first detection unit 204 detects return light in which the illumination light irradiated from the measurement probe 3 is reflected and/or scattered from the measuring target and outputs the detection result to the control unit 211. Specifically, the first detection unit 204 detects the intensity of the scattered light (spectrum) entered from the measurement probe 3 and outputs the detection result to the control unit 211. The first detection unit 204 is formed by using a spectrometer, a light receiving sensor, a condenser lens, and the like.

The second detection unit, 205 is realized by having the similar structure to that of the first detection unit 204. The second detection unit 205 detects the return light in which the illumination light irradiated from the measurement probe 3 is reflected and/or scattered from the measuring target and outputs the detection result to the control unit 211.

The third detection unit 206 is realized by having the similar structure to that of the first detection unit 204. The third detection unit 206 detects the return light in which the illumination light irradiated from the measurement probe 3 is reflected and/or scattered from the measuring target and outputs the detection result to the control unit 211.

The fourth detection unit 207 is realized by having the similar structure to that of the first detection unit 204. The fourth detection unit 207 detects the return light in which the illumination light irradiated from the measurement probe 3 is reflected and/or scattered from the measuring target and outputs the detection result to the control unit 211.

The input unit 208 receives an input of a command signal for instructing the bio-optical measurement apparatus 2 to be started, a command signal for instructing the bio-optical measurement apparatus 2 to start measuring the measuring target, a command signal for instructing calibration processing, and the like, and then, the input unit 208 outputs the command signals to the control unit 211. The input unit 208 is realized by using a push-type switch, a touch panel, and the like.

The output unit 209 outputs various information on the bio-optical measurement apparatus 2, such as the measurement result of the measuring target, under the control of the control unit 211. The output unit 209 is realized by using a display such as a liquid crystal display and an organic electro luminescence (EL) display, a speaker, and the like.

The recording unit 210 records various programs for operating the bio-optical measurement apparatus 2, various data and various parameters to be used for optical measurement processing, and the like. The recording unit 210 temporarily records information under processing by the bio-optical measurement apparatus 2. Also, the recording unit 210 records the measurement result of the measuring target by the bio-optical measurement apparatus 2. The recording unit 210 is realized by using a volatile memory, a non-volatile memory, and the like. The recording unit 210 may be formed by using a memory card and the like attached from outside the bio-optical measurement apparatus 2.

The control unit 211 totally controls the bio-optical measurement apparatus 2 by transferring the command information and the data corresponding to each element of the bio-optical measurement apparatus 2. The control unit 211 is configured by using a central processing unit (CPU) and the like. The control unit 211 includes a determination unit 211a and a calculation unit 211b.

The determination unit 211a determines whether the detection result detected by the fourth detection unit 207 is equal to or more than a predetermined threshold. When the decrease in the detection result detected by the fourth detection unit 207 is equal to or more than the predetermined threshold, the determination unit 211a determines that the distal end face of the measurement probe 3 contacts the measuring target. On the other hand, when the decrease in the detection result detected by the fourth detection unit 207 is not equal to or more than the predetermined threshold, the determination unit 211a determines that the distal end face of the measurement probe 3 does not contact the measuring target.

The calculation unit 211b performs a plurality of calculating processes based on the detection results respectively detected by the first detection unit 204, the second detection unit 205, and the third detection unit 206. Then, the calculation unit 211b calculates a characteristic value regarding the characteristics of the measuring target.

Configuration of Measurement Probe 3

Figure 3:
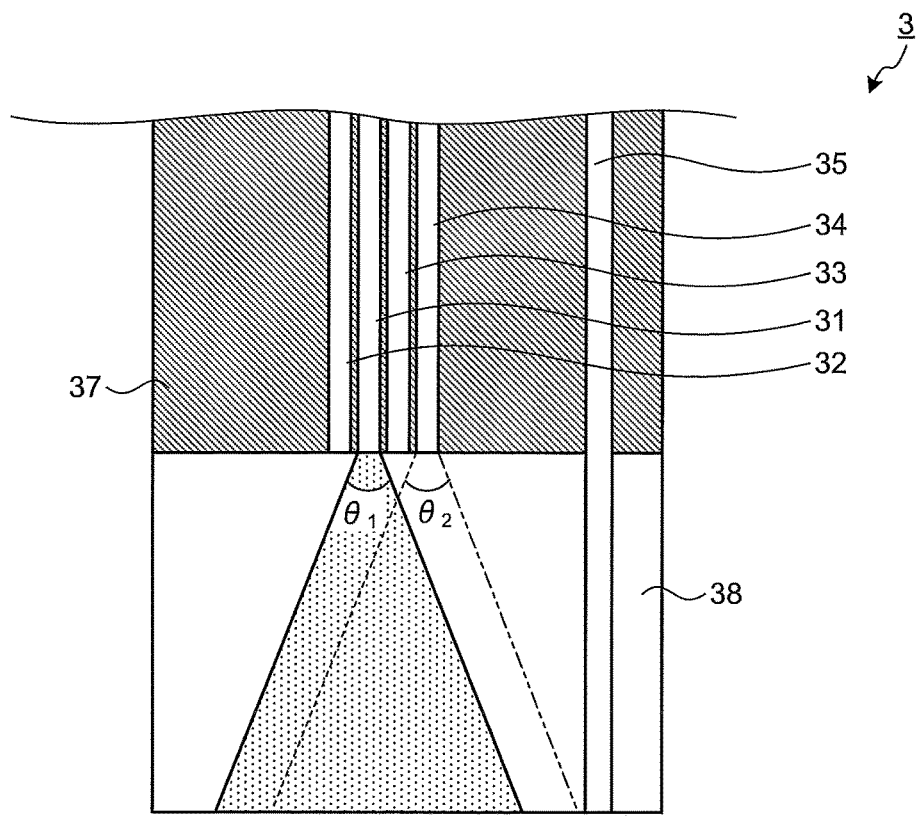
FIG. 3 is a cross-sectional diagram of a measurement probe according to the first embodiment of the present invention.
Figure 4:
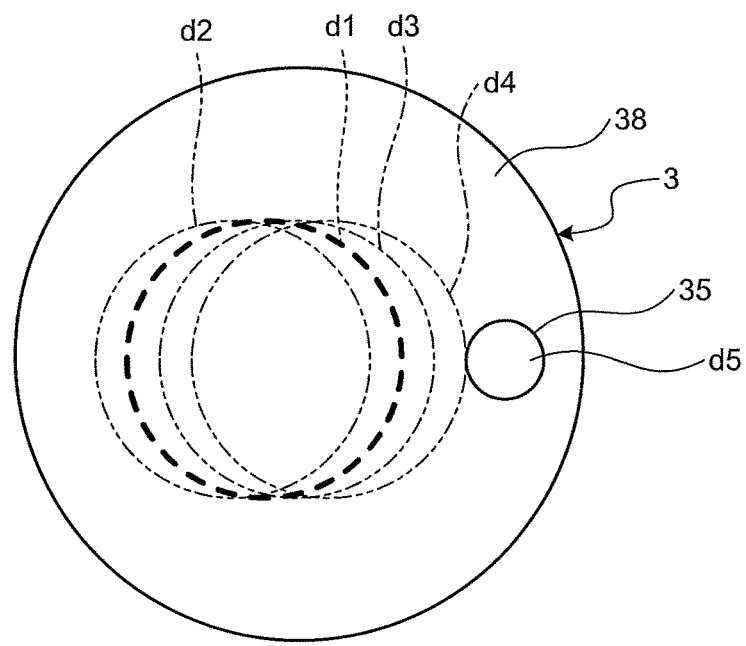
FIG. 4 is a front view of the measurement probe according to the first embodiment of the present invention viewed from a side of a distal end of the measurement probe.

Next, the configuration of the measurement probe 3 will be described. A case will be described below where the number of detecting fibers is three. However, the same can be applied to a case where there is a plurality of detecting fibers in addition to the three detecting fibers. FIG. 3 is a cross-sectional diagram of the measurement probe 3. FIG. 4 is a front view of the measurement probe 3 viewed from a side of the distal end.

The measurement probe 3 illustrated in FIGS. 2 to 4 includes an illuminating fiber 31, a first light receiving fiber 32 (first light receiving channel), a second light receiving fiber 33 (second light receiving channel), a third light receiving fiber 34 (third light receiving channel), and a contact detecting fiber 35 for passing through the measurement probe 3. The contact detecting fiber 35 detects a contact of the distal end face of the measurement probe 3 relative to the body tissues. The measurement probe 3 includes a flexible part 36 having one end detachably connected to the connector unit 203 of the bio-optical measurement apparatus 2 and having flexibility, a fiber holding unit 37 which is connected to another end of the flexible part 36 and holds the illuminating fiber 31, the first light receiving fiber 32, the second light receiving fiber 33, the third light receiving fiber 34, and the contact detecting fiber 35, and a rod lens 38 (optical element) which is provided at the distal end of the fiber holding unit 37. The contact detecting fiber 35 is inserted in and exposed from the rod lens 38. When the flexible part 36 is connected to the connector unit 203, the illuminating fiber 31, the first light receiving fiber 32, the second light receiving fiber 33, the third light receiving fiber 34, and the contact detecting fiber 35 are respectively connected to the light source unit 202, the first detection unit 204, the second detection unit 205, the third detection unit 206, and the fourth detection unit 207. Also, a connection mechanism which is connected to the connector unit 203 and is not shown is provided at one end of the flexible part 36.

The illuminating fiber 31 is realized by using an optical fiber and irradiates the measuring target with the illumination light via the rod lens 38. The illumination light is entered from the light source unit 202 via the connector unit 203. The illuminating fiber 31 is a bundle of one or more optical fibers.

The first light receiving fiber 32 is realized by using the optical fiber. The first light receiving fiber 32 detects (receives) the return light of the illumination light reflected and/or scattered from the measuring target via the rod lens 38 and propagates the return light to the first detection unit 204.

The second light receiving fiber 33 is realized by using the optical fiber. The second light receiving fiber 33 detects the return light of the illumination light reflected and/or scattered from the measuring target via the rod lens 38 and propagates the return light to the second detection unit 205.

The third light receiving fiber 34 is realized by using the optical fiber. The third light receiving fiber 34 detects the return light of the illumination light reflected and/or scattered from the measuring target via the rod lens 38 and propagates the return light to the third detection unit 206.

The contact detecting fiber 35 is realized by using the optical fiber. The contact detecting fiber 35 receives the return light of the illumination light and propagates the return light to the fourth detection unit 207. Also, the contact detecting fiber 35 detects the contact of the distal end face of the measurement probe 3 with the measuring target (body tissues) by receiving the return light of the illumination light. The contact detecting fiber 35 is inserted in a hole which has been previously provided in the rod lens 38 and is provided on the side of the distal end of the rod lens 38. The contact detecting fiber 35 may be integrally liquid-tightly formed of a resin and the like after being mounted in the rod lens 38. One end of the rod lens 38 is cut into a D shape.

Also, as illustrated in FIGS. 3 and 4, regarding the contact detecting fiber 35, a detection region d5 of the contact detecting fiber 35 on the distal end face of the rod lens 38 where the illumination light irradiated by the illuminating fiber 31 and the return light reflected from the measuring target pass through is arranged at a position outside an illumination region d1 irradiated by the illuminating fiber 31. In addition, the contact detecting fiber 35 is arranged in a position where the detection region d5 of the contact detecting fiber 35 is located outer than each of detection regions d2 to d4 of the first light receiving fiber 32, the second light receiving fiber 33, and the third light receiving fiber 34. In addition, the contact detecting fiber 35 is arranged such that a distance between the distal end of the contact detecting fiber 35 and the distal end of the illuminating fiber 31 in a direction along the distal end face of the rod lens 38 becomes longer than each of distances between the distal ends of the first light receiving fiber 32, the second light receiving fiber 33, and the third light receiving fiber 34 and the distal end of the illuminating fiber 31. Also, the contact detecting fiber 35 is arranged such that a distance between the distal end of the contact detecting fiber 35 and the distal end face of the rod lens 38 becomes shorter than each of distances between the distal ends of the first light receiving fiber 32, the second light receiving fiber 33, and the third light receiving fiber 34 and the distal end face of the rod lens 38.

The fiber holding unit 37 arranges the distal ends of the illuminating fiber 31, the first light receiving fiber 32, the second light receiving fiber 33, and the third light receiving fiber 34 in an arbitrary array and holds them. In FIG. 3, a case will be illustrated where the illuminating fiber 31, the first light receiving fiber 32, the second light receiving fiber 33, and the third light receiving fiber 34 are aligned in a straight line. Also, the fiber holding unit 37 holds the illuminating fiber 31, the first light receiving fiber 32, the second light receiving fiber 33, and the third light receiving fiber 34 so that optical axes of them are arranged in parallel to one another. In addition, the fiber holding unit 37 holds the contact detecting fiber 35. The fiber holding unit 37 is realized by using glass, resin, or metal.

The rod lens 38 is provided at the distal end of the fiber holding unit 37. The rod lens 38 is realized by using glass, plastic, and the like having predetermined permeability. Specifically, a glass rod or plastic rod which has light transmission properties and does not have a light pass bending effect as that of the lens, or an optical lens or a refractive index distribution type lens (GRIN lens) having curvature is used for the rod lens 38. When a lens is used for the rod lens 38, the lens is arranged such that a focal plane of the lens is located at the respective distal ends of the illuminating fiber 31, the first light receiving fiber 32, the second light receiving fiber 33, and the third light receiving fiber 34. The rod lens 38 has a cylindrical shape so that distances between the distal ends of the illuminating fiber 31, the first light receiving fiber 32, the second light receiving fiber 33, and the third light receiving fiber 34 and the measuring target become constant. It is appropriate that the distal end face of the rod lens 38 is obliquely formed relative to the optical axis of the illuminating fiber 31 so that the illumination light from the illuminating fiber 31 reflected from the distal end face of the rod lens 38 by Fresnel reflection does not directly enter all the detecting fibers. For the description, the surface is indicated by a surface perpendicular to the optical axis of the illuminating fiber 31 in the drawings.

Figure 5:
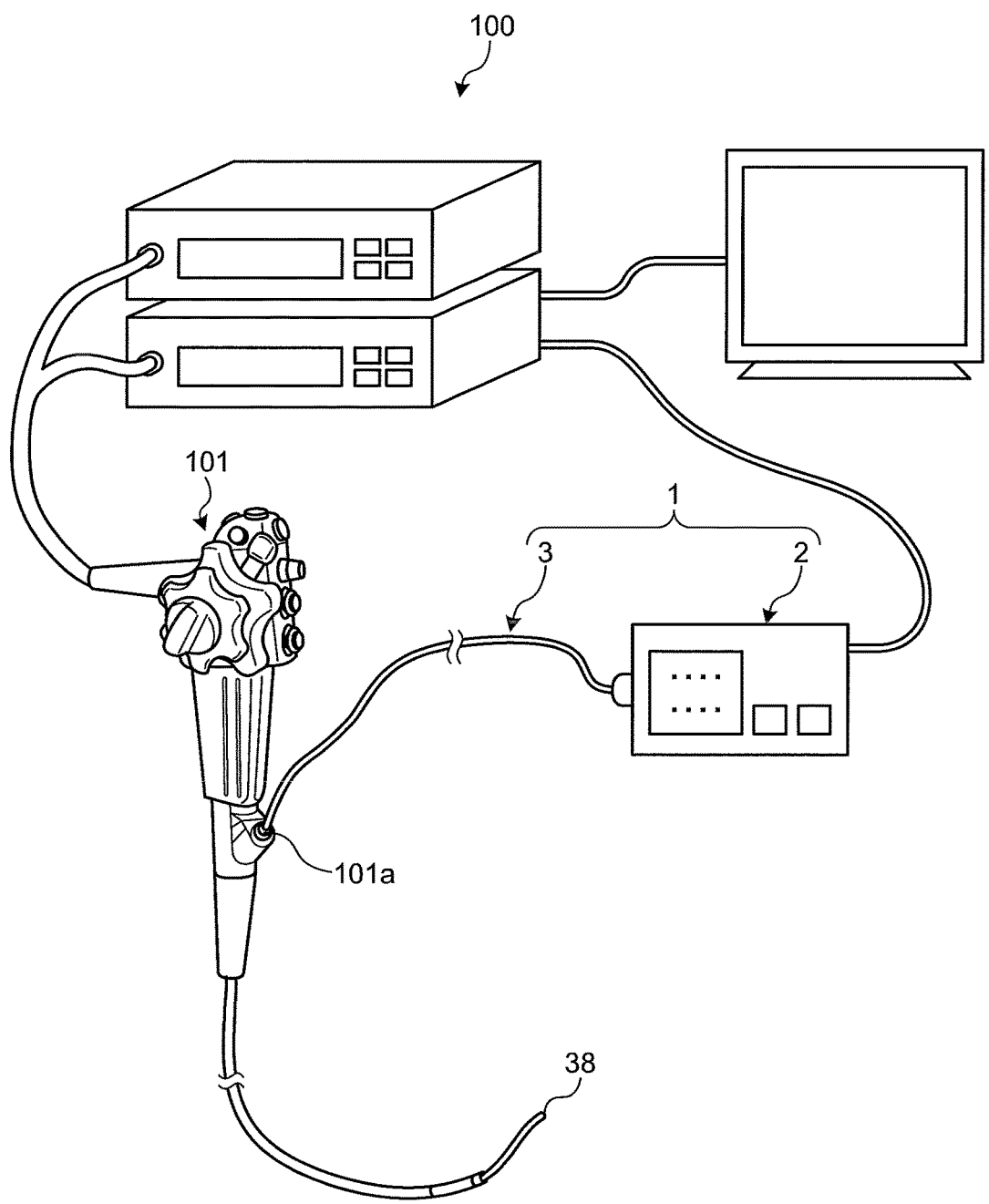
FIG. 5 is a diagram of a state where the bio-optical measurement system according to the first embodiment of the present invention is used in an endoscope system.

As illustrated in FIG. 5, in the bio-optical measurement system 1 formed as described above, the measurement probe 3 is inserted into the subject via a treatment tool channel 101a provided in an endoscope apparatus 101 (endoscope scope) of an endoscope system 100. The illuminating fiber 31 irradiates the measuring target with the illumination light. The first light receiving fiber 32, the second light receiving fiber 33, the third light receiving fiber 34 respectively detect the return light of the illumination light reflected and/or scattered from the measuring target at different scattering angles and respectively propagate the return light to the first detection unit 204, the second detection unit 205, and the third detection unit 206. After that, the calculation unit 211b calculates the characteristic value of the measuring target based on the detection results respectively detected by the first detection unit 204, the second detection unit 205, and the third detection unit 206.

Processing of Bio-Optical Measurement System

Figure 6:
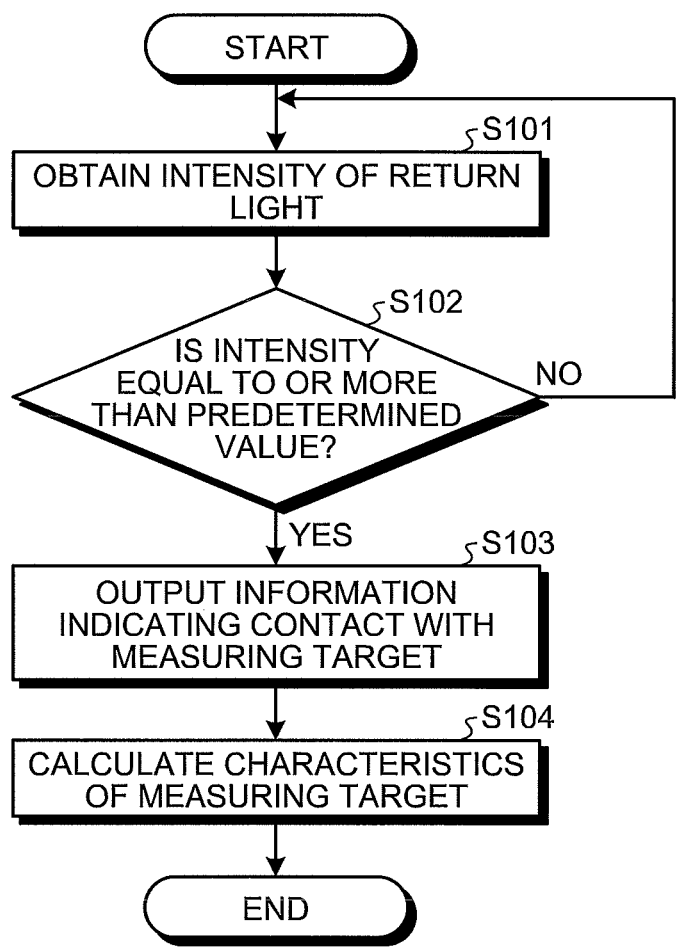
FIG. 6 is a flowchart of an outline of processing performed by the bio-optical measurement system according to the first embodiment of the present invention.
Figure 7A:
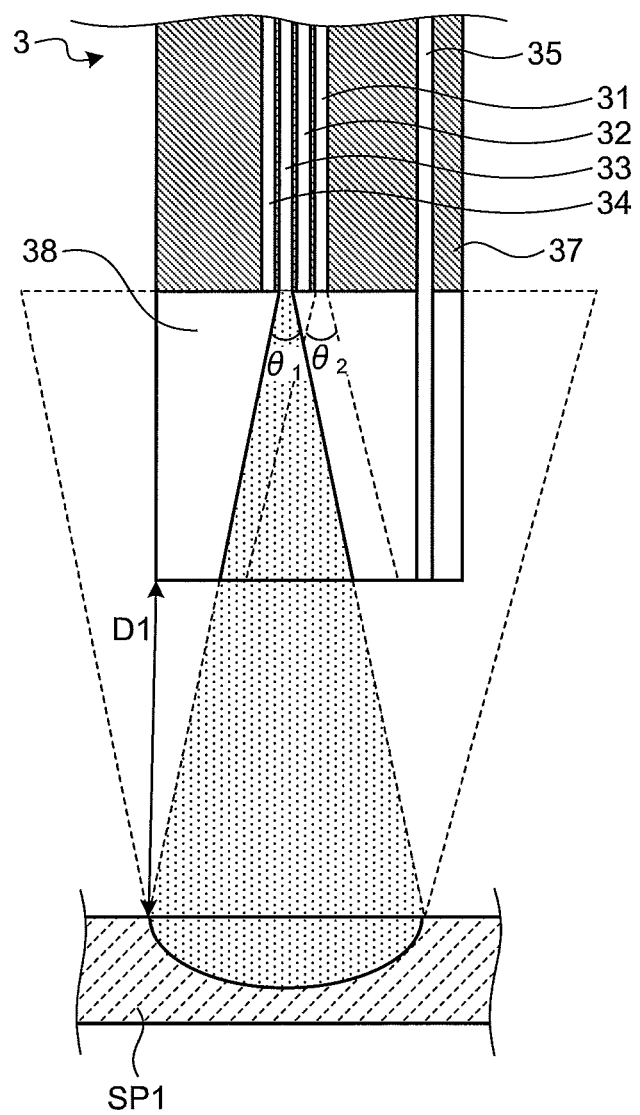
FIG. 7A is a schematic diagram of a state where a measuring target is measured by using the measurement probe according to the first embodiment of the present invention.
Figure 7B:
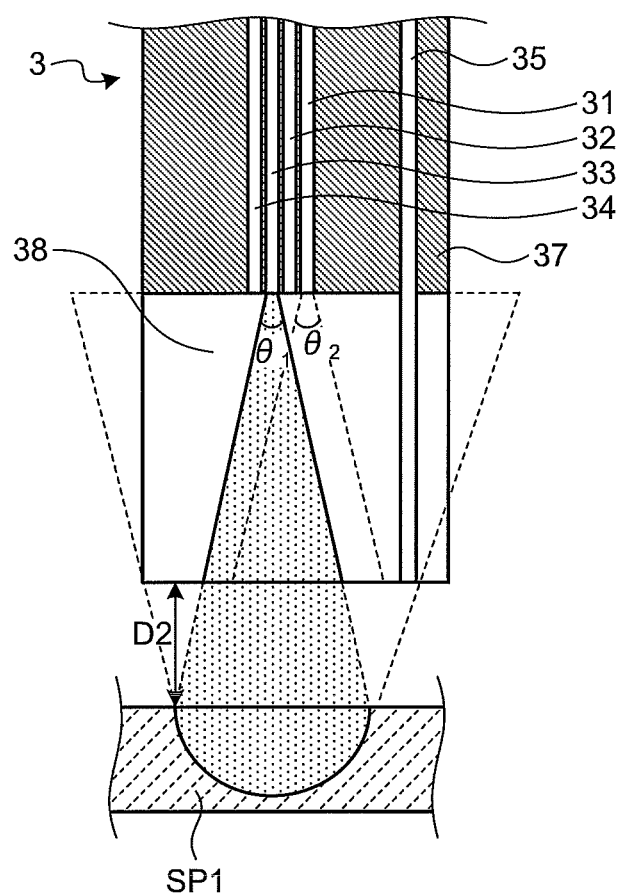
FIG. 7B is a schematic diagram of a state where the measuring target is measured by using the measurement probe according to the first embodiment of the present invention.
Figure 7C:
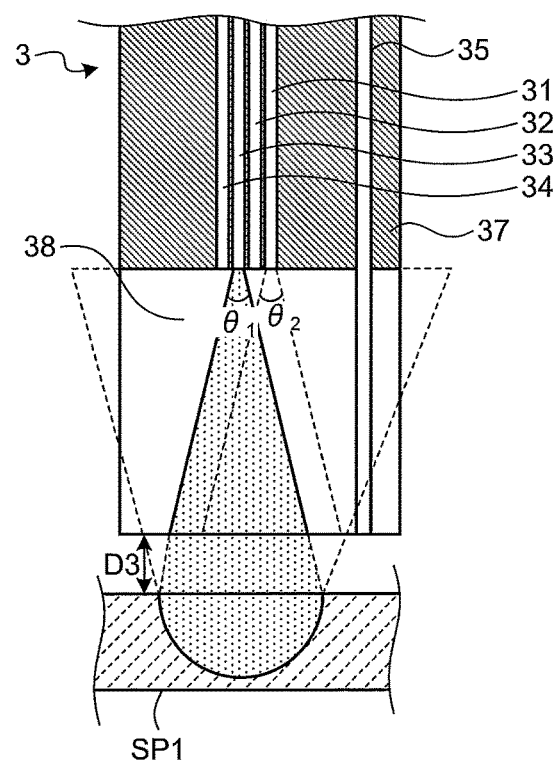
FIG. 7C is a schematic diagram of a state where the measuring target is measured by using the measurement probe according to the first embodiment of the present invention.
Figure 7D:
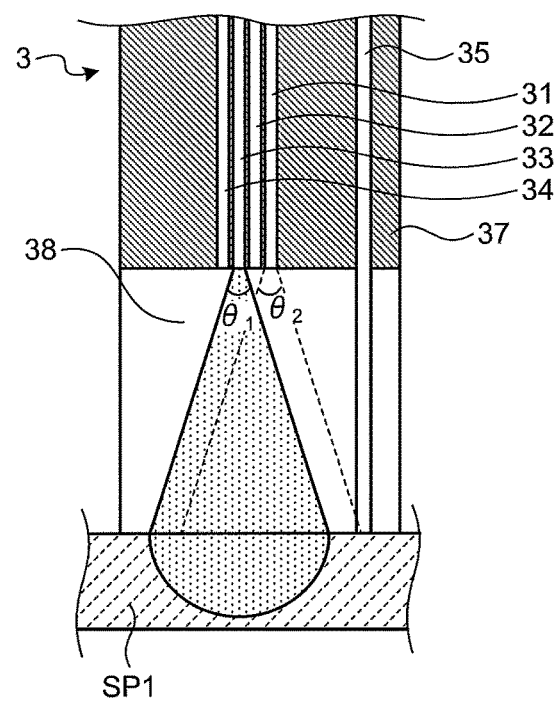
FIG. 7D is a schematic diagram of a state where the measuring target is measured by using the measurement probe according to the first embodiment of the present invention.

Next, processing performed by the above-mentioned bio-optical measurement system 1 will be described. FIG. 6 is a flowchart of an outline of the processing performed by the bio-optical measurement system 1.

First, as illustrated in FIG. 6, the determination unit 211a obtains the intensity of the return light of the illumination light detected by the fourth detection unit 207 via the contact detecting fiber 35 (step S101) and determines whether the intensity of the return light of the illumination light obtained from the fourth detection unit 207 is equal to or more than a predetermined value (step S102). When the determination unit 211a has determined that the intensity of the return light of the illumination light obtained from the fourth detection unit 207 is equal to or more than the predetermined value (step S102: Yes), the bio-optical measurement system 1 proceeds to step S103 to be described. On the other hand, when the determination unit 211a has determined that the intensity of the return light of the illumination light obtained from the fourth detection unit 207 is not equal to or more than the predetermined value (step S102: No), the bio-optical measurement system 1 returns to step S101.

Figure 8:
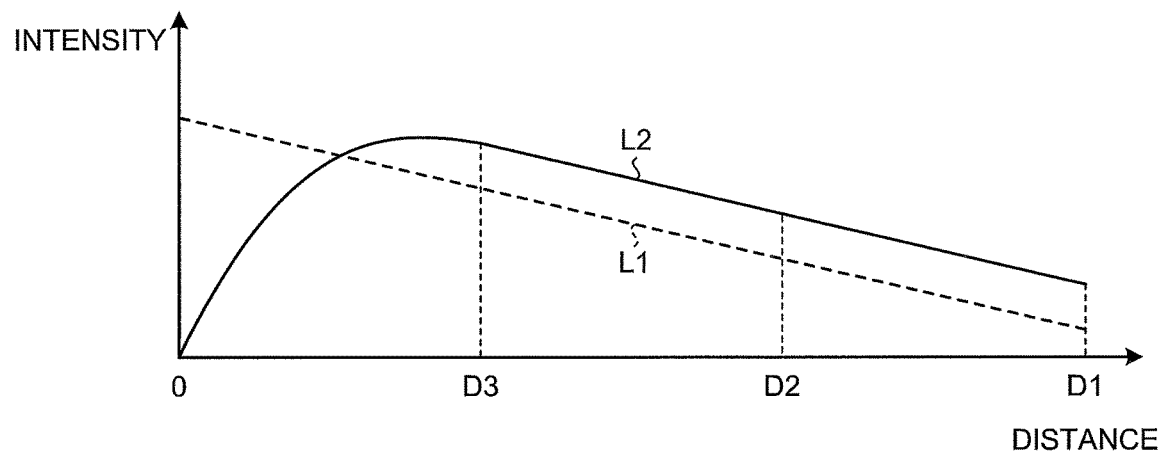
FIG. 8 is a diagram of relationship between intensities of the return light respectively detected by a first detection unit and a fourth detection unit in the states illustrated in FIGS. 7A to 7D and a distance between the distal end of the measurement probe and the measuring target.

FIGS. 7A to 7D are schematic diagrams of a state where the measuring target is measured by using the measurement probe 3. FIG. 8 is a diagram of a relationship between the intensities of the return light respectively detected by the first detection unit 204 and the fourth detection unit 207 in the states illustrated in FIGS. 7A to 7D and a distance between the distal end of the measurement probe 3 and the measuring target. Also, in FIGS. 7A to 7D, when the illumination light is irradiated from the illuminating fiber 31, the return light includes not only the reflection from a surface of the measuring target, but also includes reflection and/or scattering inside the measuring target. However, for purposes of illustration and not limitation, the return light reflected and scattered from the surface of the measuring target is schematically illustrated. In FIG. 8, the vertical axis indicates the intensity (value), and the horizontal axis indicates the distance between the distal end of the measurement probe 3 and the measuring target. In addition, in FIG. 8, the curved line L1 indicates the detection result of the first detection unit 204, and the curved line L2 indicates the detection result of the fourth detection unit 207.

As illustrated in FIGS. 7A to 7D and FIG. 8, as the measurement probe 3 gradually gets closer to a measuring target SP1 (FIG. 7A→4 FIG. 7B→FIG. 7C), values respectively detected by the first detection unit 204 and the fourth detection unit 207 gradually increase. Specifically, the return light respectively detected by the first light receiving fiber 32 and the contact detecting fiber 35 is light in which the illumination light irradiated by the illuminating fiber 31 is spread with a predetermined angle. At the same time, since the scatter occurs on the surface of the measuring target SP1, the light becomes spread light diffused wider than that in a case where the light has been irradiated from the illuminating fiber 31.

That is, the intensities of the return light respectively detected by the first light receiving fiber 32 and the contact detecting fiber 35 significantly depend on a distance between the measurement probe 3 and the measuring target SP1. Therefore, the intensity of the return light detected by the first light receiving fiber 32 gradually increases as the measurement probe 3 gets closer to the measuring target SP1 (distance D1→distance D2→distance D3). On the other hand, the intensity of the return light detected by the contact detecting fiber 35 sharply decreases just before the measurement probe 3 contacts the measuring target SP1. As illustrated above-mentioned FIG. 4, regarding the contact detecting fiber 35, the detection region d5 for detecting the return light does not overlap with an illumination region d1 of the illuminating fiber 31 so that this phenomenon occurs. In addition, when the intensity of the return light detected by the contact detecting fiber 35 is compared with that detected by the first light receiving fiber 32, the intensity of the return light of the contact detecting fiber 35 previously decreases. This phenomenon is caused by a difference between the distances of the detection region of the contact detecting fiber 35 and the illumination region of the illuminating fiber 31.

In this way, when the decrease in the intensity of the return light detected by the fourth detection unit 207 via the contact detecting fiber 35 is equal to or more than the predetermined value, the determination unit 211a determines that the distal end face of the measurement probe 3 contacts the measuring target SP1. On the other hand, when the decrease in the intensity of the return light detected by the fourth detection unit 207 via the contact detecting fiber 35 is not equal to or more than the predetermined value, the determination unit 211a determines that the distal end face of the measurement probe 3 does not contact the measuring target SP1. Specifically, the determination unit 211a compares the intensities of the two beams of temporally successive return light detected by the fourth detection unit 207 with each other and determines whether the decreased value or gradient is equal to or more than the predetermined value when the intensity of the return light has decreased. Accordingly, the determination unit 211a determines whether the distal end face of the measurement probe 3 contacts the measuring target SP1. When the intensity of the return light of the illumination light detected by the fourth detection unit 207 continues to decrease for a certain time after it has continued to increase for a certain time, the determination unit 211a may determine that the distal end face of the measurement probe 3 contacts the measuring target SP1.

The procedure returns to FIG. 6, and the description after step S103 will be continued.

In step S103, the control unit 211 makes the output unit 209 output information indicating that the distal end of the measurement probe 3 has contacted the measuring target SP1. Specifically, the control unit 211 makes the output unit 209 output an icon and the information indicating that the distal end of the measurement probe 3 has contacted the body tissues. The control unit 211 may make the output unit 209 output as voice and the like for indicating that the distal end of the measurement probe 3 has contacted the body tissues.

Subsequently, the calculation unit 211b calculates the characteristics of the measuring target SP1 based on the values of the return light from the measuring target SP1 respectively detected by the first detection unit 204, the second detection unit 205, and the third detection unit 206 (step S104). In this case, the output unit 209 may output the calculation result by the calculation unit 211b. After step S104, the bio-optical measurement system 1 terminates this procedure.

According to the first embodiment described above, since the contact detecting fiber 35 is arranged such that the detection region d5 of the contact detecting fiber 35 is arranged outside the illumination region d1 of the illuminating fiber 31, it is possible to determine whether the distal end face of the measurement probe 3 surely contacts the body tissues.

Also, according to the first embodiment, when the decrease in the intensity of the return light detected by the fourth detection unit 207 via the contact detecting fiber 35 is equal to or more than the predetermined value, the determination unit 211a determines that the distal end face of the measurement probe 3 contacts the measuring target SP1. On the other hand, when the decrease in the intensity of the return light detected by the fourth detection unit 207 via the contact detecting fiber 35 is not equal to or more than the predetermined value, the determination unit 211a determines that the distal end face of the measurement probe 3 does not contact the measuring target SP1. Accordingly, it is possible to determine whether the distal end face of the measurement probe 3 surely contacts the body tissues.

In the first embodiment, the distal end face of the contact detecting fiber 35 has been exposed. However, a different optical member such as cover glass may be provided, for example, on the distal end face of the contact detecting fiber 35 and the rod lens 38.

First Modification of First Embodiment

Figure 9:
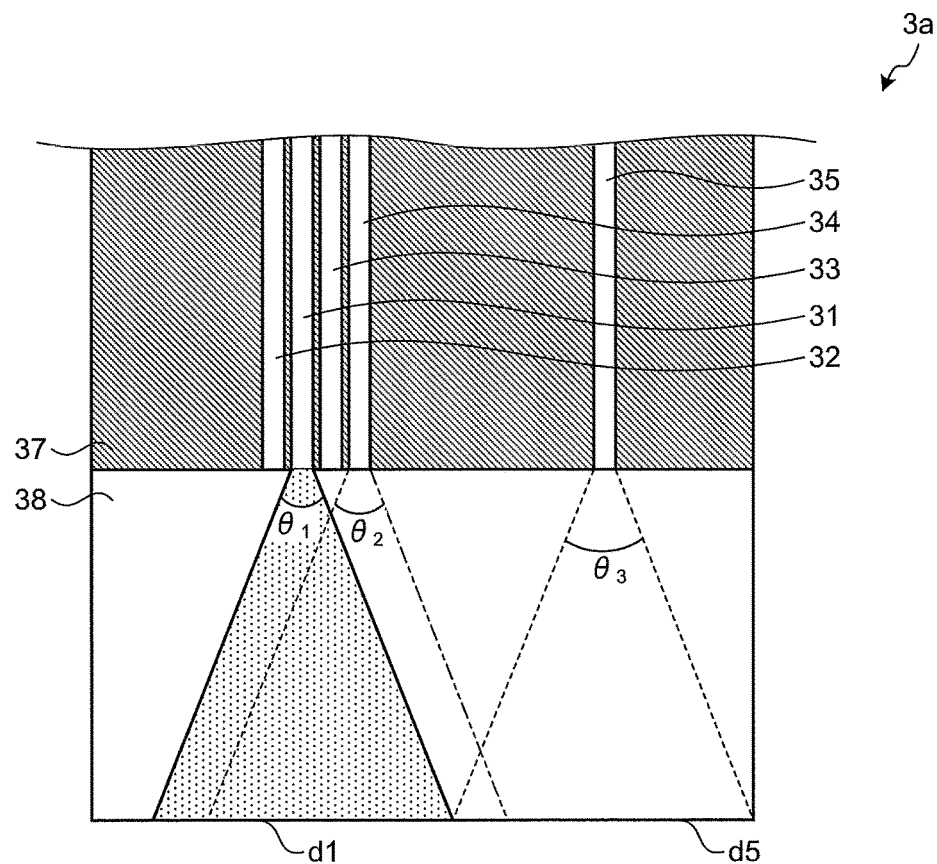
FIG. 9 is a cross-sectional diagram of a measurement probe according to a first modification of the first embodiment of the present invention.

Next, a first modification of the first embodiment will be described. FIG. 9 is a cross-sectional diagram of a measurement probe according to the first modification of the first embodiment.

In a measurement probe 3a illustrated in FIG. 9, the contact detecting fiber 35 is held by the fiber holding unit 37 in the same line as each of the first light receiving fiber 32, the second light receiving fiber 33, and the third light receiving fiber 34. Specifically, the contact detecting fiber 35 is held by the fiber holding unit 37 so that a distance between the distal end and the distal end face of the rod lens 38 is the same as a distance between each of distal ends of the first light receiving fiber 32, the second light receiving fiber 33, and the third light receiving fiber 34 and the distal end face of the rod lens 38. In addition, the contact detecting fiber 35 detects the return light of the illumination light irradiated by the illuminating fiber 31 via the rod lens 38. Also, the contact detecting fiber 35 is held by the fiber holding unit 37 so that the detection region d5 of the contact detecting fiber 35 on the distal end face of the measurement probe 3a (numerical aperture $\theta_3$) is arranged outside the illumination region d1 on the distal end face of the measurement probe 3a irradiated by the illuminating fiber 31 (numerical aperture $\theta_1$).

According to the first modification of the first embodiment described above, the measurement probe 3a can be manufactured with a simple structure. In addition, the illuminating fiber 31, the first light receiving fiber 32, the second light receiving fiber 33, the third light receiving fiber 34, and the contact detecting fiber 35 of the measurement probe 3a can be integrated together by using a single fiber bundle.

Second Modification of First Embodiment

Figure 10:
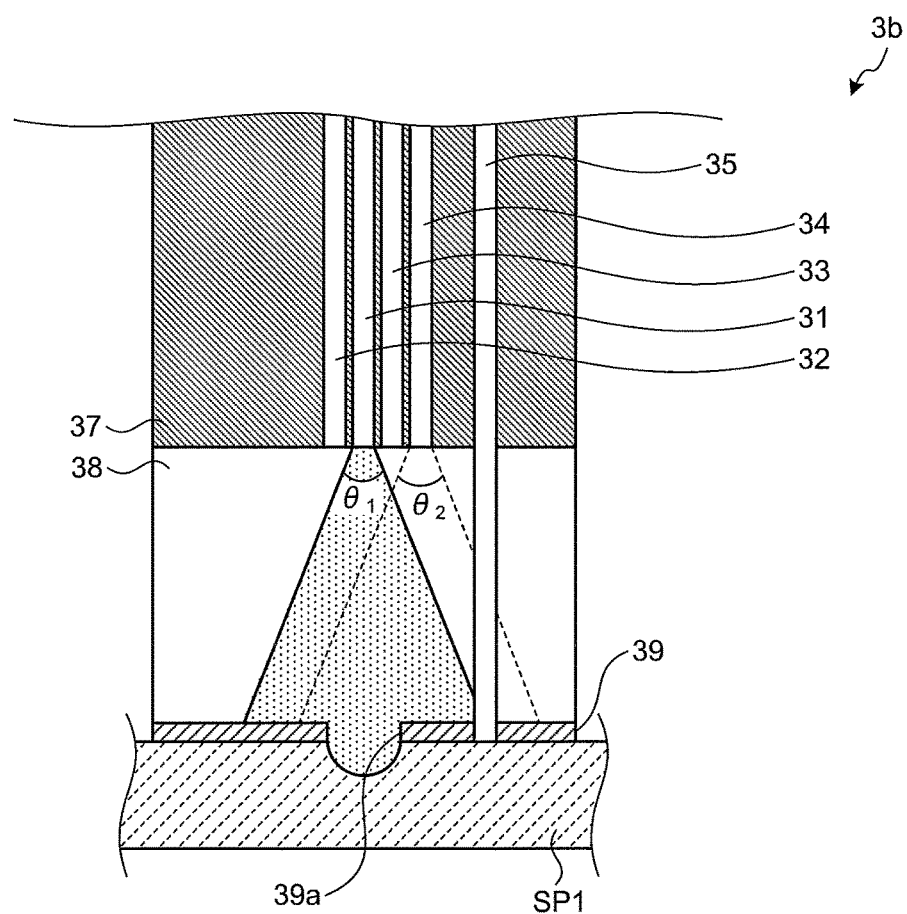
FIG. 10 is a cross-sectional diagram of a measurement probe according to a second modification of the first embodiment of the present invention.

Next, a second modification of the first embodiment will be described. FIG. 10 is a cross-sectional diagram of a measurement probe according to the second modification of the first embodiment.

A measurement probe 3b illustrated in FIG. 10 further includes a diaphragm 39 for shielding a part of the illumination light irradiated by the illuminating fiber 31 in addition to the elements of the first embodiment described above.

The diaphragm 39 has an annular shape and is formed by using a light shielding member. The diaphragm 39 includes an aperture part 39a, and the measuring target SP1 is irradiated with a part of the illumination light irradiated by the illuminating fiber 31 by the aperture part 39a. The diaphragm 39 isolates an illumination region of the illumination light irradiated by the illuminating fiber 31 from a detection region of the contact detecting fiber 35. Specifically, the diaphragm 39 shields a part (most part) of the illumination light irradiated by the illuminating fiber 31 not to enter the contact detecting fiber 35.

According to the second modification of the first embodiment described above, since the diaphragm 39 isolates the illumination region of the illumination light irradiated by the illuminating fiber 31 from the detection region detected by the contact detecting fiber 35, the measurement probe 3b can be miniaturized. In addition, the size of the illumination region by the illuminating fiber 31 can be freely set regardless of the numerical aperture of the illuminating fiber 31.

Second Embodiment

Next, a second embodiment of the present invention will be described. A bio-optical measurement system according to the second embodiment includes a measurement probe having a configuration different from that of the first embodiment which has been mentioned above. Specifically, the measurement probe according to the second embodiment includes a plurality of contact detecting fibers. Therefore, in the following description, after the configuration of the measurement probe according to the second embodiment is described, processing performed by the bio-optical measurement system according to the second embodiment will be described. The same reference signs are used to designate the same elements as those of the above-mentioned bio-optical measurement system 1 according to the first embodiment, and the explanation thereof will be omitted.

Configuration of Measurement Probe

Figure 11:
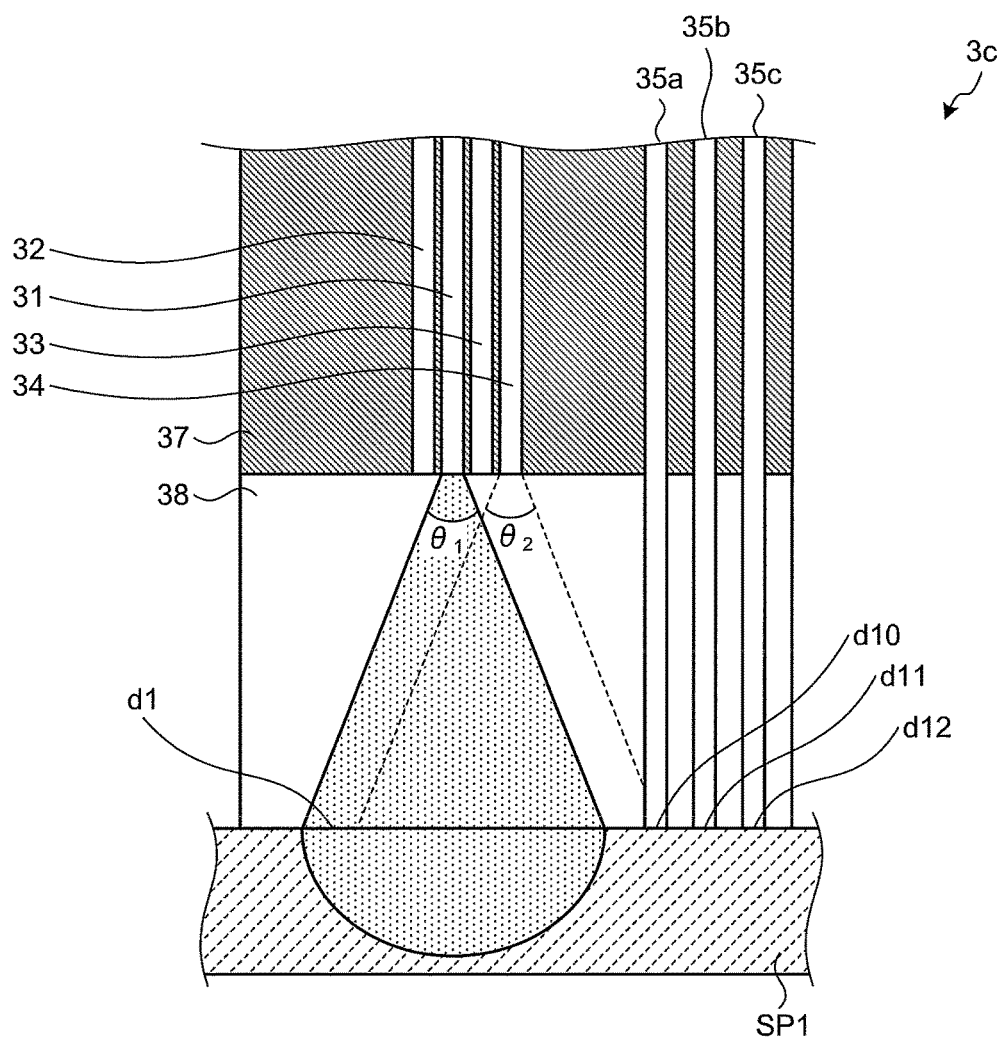
FIG. 11 is a cross-sectional diagram of a measurement probe according to a second embodiment of the present invention.

FIG. 11 is a cross-sectional diagram of the measurement probe according to the second embodiment. A measurement probe 3c illustrated in FIG. 11 includes a plurality of contact detecting fibers 35a to 35c in addition to the elements of the above-mentioned measurement probe 3 according to the first embodiment described above.

The plurality of contact detecting fibers 35a to 35c is realized by using optical fibers. The contact detecting fibers 35a to 35c detect return light of illumination light and propagate the return light to a fourth detection unit 207. The plurality of contact detecting fibers 35a to 35c is inserted into a hole which has been previously provided in a rod lens 38 and is provided on a side of a distal end of the rod lens 38. The plurality of contact detecting fibers 35a to 35c may be integrally formed of a resin and the like after being mounted in the rod lens 38. One end of the rod lens 38 is cut into a D shape.

Also, each of the plurality of contact detecting fibers 35a to 35c is held by a fiber holding unit 37 so that detection regions d10 to d12 on the distal end face of the rod lens 38 are arranged at positions outside an illumination region d1 irradiated by an illuminating fiber 31. In a fourth detection unit 207, a plurality of light receiving elements corresponding to the plurality of contact detecting fibers 35a to 35c may be provided, and a single light receiving element may detect the intensities of the return light of the illumination light respectively received by the plurality of contact detecting fibers 35a to 35c by periodically switching the fiber to be detected.

Processing of Bio-Optical Measurement System

Figure 12:
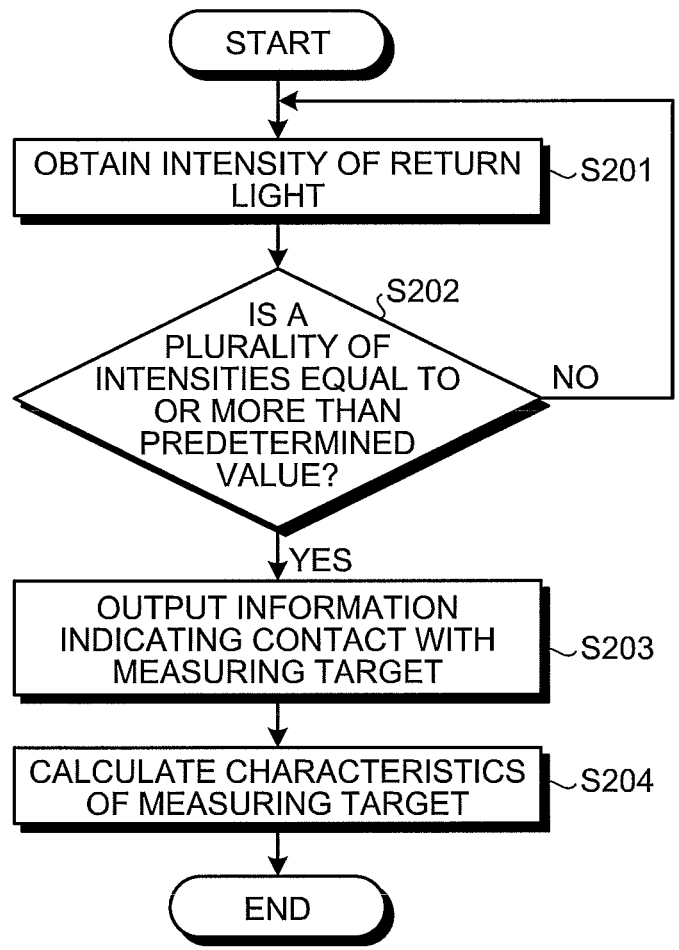
FIG. 12 is a flowchart of an outline of processing performed by a bio-optical measurement system according to the second embodiment of the present invention.

Next, the processing performed by the bio-optical measurement system 1 according to the second embodiment will be described. FIG. 12 is a flowchart of an outline of the processing performed by the bio-optical measurement system 1.

First, as illustrated in FIG. 12, a determination unit 211a obtains the intensities of the return light of the illumination light detected by the fourth detection unit 207 via the contact detecting fibers 35a to 35c (step S201) and determines whether the plurality of intensities obtained from the fourth detection unit 207 is equal to or more than a predetermined value (step S202). When the determination unit 211a has determined that the plurality of intensities obtained from the fourth detection unit 207 is equal to or more than the predetermined value (step S202: Yes), the bio-optical measurement system 1 proceeds to step S203 to be described. On the other hand, when the determination unit 211a has determined that the plurality of intensities obtained from the fourth detection unit 207 is not equal to or more than the predetermined value (step S202: No), the bio-optical measurement system 1 proceeds to step S201.

Figure 13:
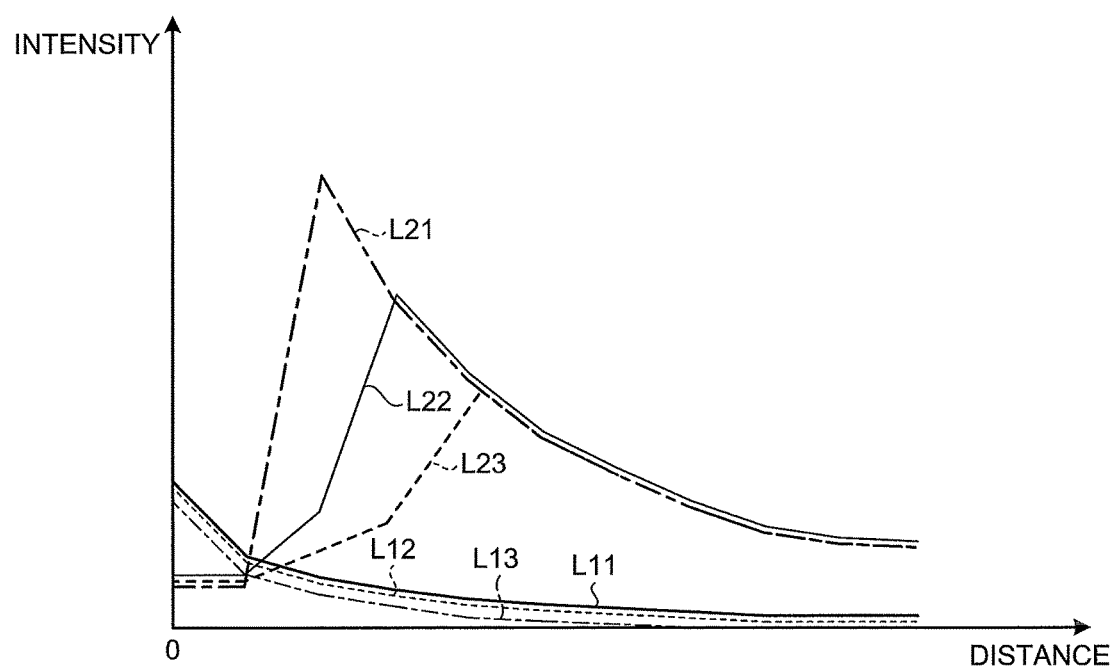
FIG. 13 is a diagram of relationship between intensities of the return light respectively detected by a first light receiving fiber, a second light receiving fiber, a third light receiving fiber, and a contact detecting fiber, and a distance between a distal end of the measurement probe and a measuring target according to the second embodiment of the present invention.

FIG. 13 is a diagram of relationship between the intensities of the return light respectively detected by the first light receiving fiber 32, the second light receiving fiber 33, the third light receiving fiber 34, and the contact detecting fibers 35a to 35c and a distance between the distal end of the measurement probe 3c and a measuring target SP1. In FIG. 13, the vertical axis indicates the intensity (value), and the horizontal axis indicates a distance between the distal end of the measurement probe 3c and the measuring target SP1. In addition, in FIG. 13, a curved line L11 indicates the intensity of the return light detected by the first light receiving fiber 32, and a curved line L12 indicates the intensity of the return light detected by the second light receiving fiber 33. A curved line L13 indicates the intensity of the return light detected by the third light receiving fiber 34, and a curved line L21 indicates the intensity of the return light detected by the contact detecting fiber 35a. A curved line L22 indicates the intensity of the return light detected by the contact detecting fiber 35b, and a curved line L23 indicates the intensity of the return light detected by the contact detecting fiber 35c.

As illustrated in FIG. 13, as the measurement probe 3c gradually gets closer to the measuring target SP1, the intensities of the return light respectively detected by the first light receiving fiber 32, the second light receiving fiber 33, the third light receiving fiber 34, and the contact detecting fibers 35a to 35c gradually increase. Specifically, the return light respectively detected by the first light receiving fiber 32, the second light receiving fiber 33, the third light receiving fiber 34, and the contact detecting fibers 35a to 35c is light in which the illumination light irradiated by the illuminating fiber 31 is spread with a predetermined angle. At the same time, since the scatter occurs on the surface of the measuring target SP1, the light becomes spread light diffused wider than that in a case where the light has been irradiated from the illuminating fiber 31.

That is, the intensities of the return light respectively detected by the first light receiving fiber 32, the second light receiving fiber 33, the third light receiving fiber 34, and the contact detecting fibers 35a to 35c significantly depend on the distance between the measurement probe 3c and the measuring target SP1. Therefore, the intensities of the return light respectively detected by the first light receiving fiber 32, the second light receiving fiber 33, and the third light receiving fiber 34 gradually increase as the measurement probe 3c gets closer to the measuring target SP1. On the other hand, the intensities of the return light detected by the contact detecting fibers 35a to 35c sharply decrease just before the measurement probe 3c contacts the measuring target SP1. The detection regions d10 to d12 of the respective contact detecting fibers 35a to 35c do not overlap with the illumination region d1 of the illuminating fiber 31, and accordingly, this phenomenon occurs.

In addition, when the intensities of the return light respectively detected by the contact detecting fibers 35a to 35c are compared with one another, positions where the intensity of the return light decreases are in an order of the distances from the illuminating fiber 31 from the longer one. This phenomenon is caused by a difference between the distances of the detection regions d10 to d12 of the respective contact detecting fibers 35a to 35c to the illumination region d1 of the illuminating fiber 31. That is, regarding the position where the intensity of the return light of the illumination light sharply decreases, the order of the decrease in the intensity of the return light becomes earlier as the distance between the detection regions d10 to d12 of the contact detecting fibers 35a to 35c and the illumination region d1 of the illuminating fiber 31 is longer.

In this way, the respective detection regions d10 to d12 of the contact detecting fibers 35a to 35c are arranged not to overlap with the illumination region d1 of the illuminating fiber 31, and the contact detecting fibers 35a to 35c respectively having a different distance from the illuminating fiber 31 to one another are arranged. Accordingly, the contact of the measurement probe 3c with the measuring target SP1 can be accurately detected. For example, according to the conventional method, when the contact state between the measurement probe 3c and the measuring target SP1 is detected by using the first light receiving fiber 32, the second light receiving fiber 33, and the third light receiving fiber 34, it is preferable to detect the contact state by providing a threshold relative to the intensity of the return light. However, variations of the intensities of the return light becomes large according to the state of the measuring target SP1, the angle between the measurement probe 3c and the measuring target SP1, the state of the illuminating fiber 31 (for example, decrease in light quantity of light source, connection state of fiber, and transmittance of fiber), and the state of the detecting fiber (for example, sensitivity of detector, connection state of fiber, and transmittance of fiber). That is, according to the conventional method, it is necessary to set the threshold of the intensity of the return light to a value in view of the above-mentioned variation. Therefore, the contact state between the measurement probe 3c and the measuring target SP1 cannot be accurately detected.

In order to address such a situation, in the second embodiment, when the decrease in the plurality of intensities of the return light respectively detected by the fourth detection unit 207 via the contact detecting fibers 35a to 35c is equal to or more than the predetermined value, the determination unit 211a determines that the distal end of the measurement probe 3c contacts the measuring target SP1. On the other hand, when the decrease in the plurality of intensities of the return light respectively detected by the fourth detection unit 207 via the contact detecting fibers 35a to 35c is not equal to or more than the predetermined value, the determination unit 211a determines that the distal end of the measurement probe 3c does not contact the measuring target SP1. As a result, the contact of the measurement probe 3c with the measuring target SP1 can be surely detected without depending on variation in the intensities of the return light respectively detected by the contact detecting fibers 35a to 35c.

Also, the distance between the measurement probe 3c and the measuring target SP1 does not always vary at fixed intervals. For example, when the positions of the measurement probe 3c and the measuring target SP1 have moved rapidly from the positions where the distance between them is short to the positions where the distance between them is long, there may be a position where the intensity of the return light sharply decreases. However, according to the third embodiment, when the positions of the measurement probe 3c and the measuring target SP1 have moved rapidly from the positions where the distance between them is short to the positions where the distance between them is long, the intensities of the return light respectively detected by the contact detecting fibers 35a to 35c vary in the same way in a case where the respective intensities of the return light of the contact detecting fibers 35a to 35c are compared with each other. On the other hand, in the state where the measurement probe 3c contacts the measuring target SP1, the intensities of the return light decrease in an order of the contact detecting fiber 35c, the contact detecting fiber 35b, and the contact detecting fiber 35a.

In this way, the determination unit 211a determines the contact state between the measurement probe 3c and the measuring target SP1 by determining the change of the intensities of the return light respectively detected by the contact detecting fibers 35a to 35c. That is, when the intensities of the return light have decreased in an order of the contact detecting fiber 35c, the contact detecting fiber 35b, and the contact detecting fiber 35a, the determination unit 211a determines that the distal end of the measurement probe 3c has contacted the measuring target SP1. On the other hand, when the respective intensities of the return light of the contact detecting fiber 35c, the contact detecting fiber 35b, and the contact detecting fiber 35a have decreased or changed in the same way, the determination unit 211a determines that the distal end of the measurement probe 3c has not contacted the measuring target SP1.

The procedure returns to FIG. 12, and the description after step S203 will be continued.

Steps S203 and S204 respectively correspond to the above-mentioned steps S103 and S104 in FIG. 6. After step S204, the bio-optical measurement system 1 terminates this procedure.

According to the second embodiment described above, since the detection regions d10 to d12 of the respective contact detecting fibers 35a to 35c are arranged at positions outside the illumination region d1 of the illuminating fiber 31, it is possible to determine whether the distal end face of the measurement probe 3c surely contacts the measuring target SP1.

Also, according to the second embodiment, when the decrease in the plurality of intensities of the return light respectively detected by the fourth detection unit 207 via the contact detecting fibers 35a to 35c is equal to or more than the predetermined value, the determination unit 211a determines that the distal end face of the measurement probe 3c contacts the measuring target SP1. On the other hand, when the decrease in the plurality of intensities of the return light respectively detected by the fourth detection unit 207 via the contact detecting fibers 35a to 35c is not equal to or more than the predetermined value, the determination unit 211a determines that the distal end face of the measurement probe 3c does not contact the measuring target SP1. As a result, the contact of the measurement probe 3c with the measuring target SP1 can be surely detected without depending on variation in the intensities of the return light respectively detected by the contact detecting fibers 35a to 35c.

In addition, according to the second embodiment, even when such foreign substances as dust adhere on the distal end face of the measurement probe 3c, it is determined whether the intensity of the return light rapidly decreases by using the contact detecting fibers 35a to 35c. Accordingly, it is possible to determine whether the distal end face of the measurement probe 3c contacts the measuring target SP1 or foreign substances adhere on the distal end face of the measurement probe 3c.

First Modification of Second Embodiment

Figure 14:
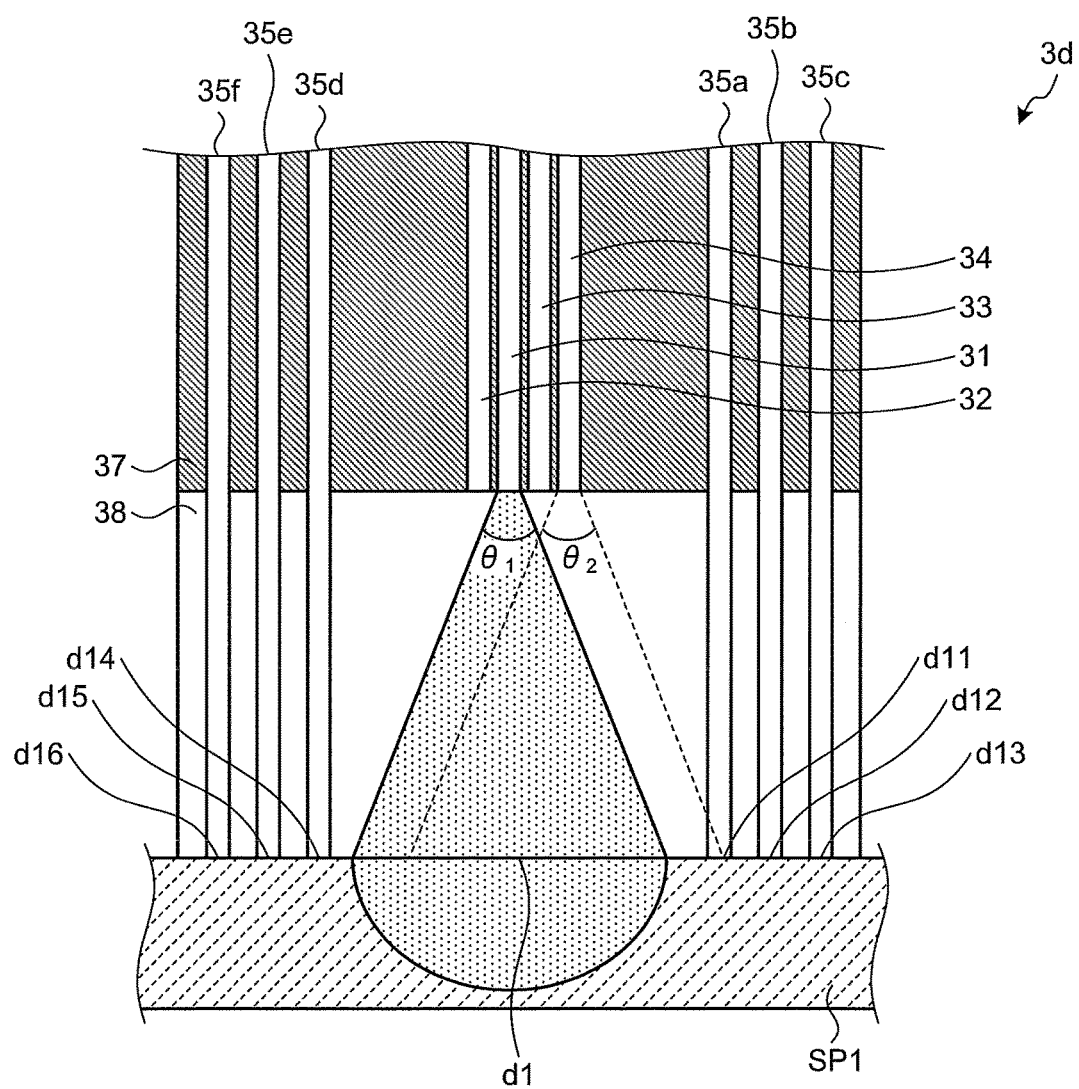
FIG. 14 is a cross-sectional diagram of a measurement probe according to a first modification of the second embodiment of the present invention.
Figure 15:
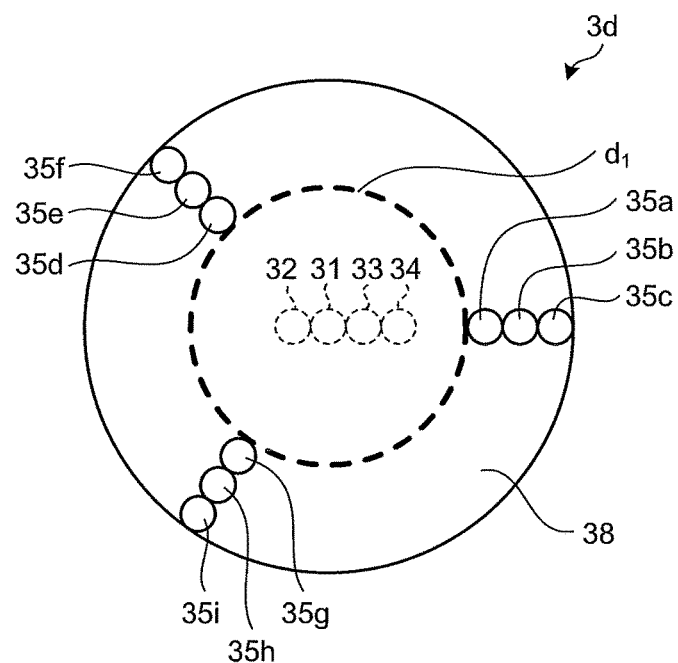
FIG. 15 is a front view of the measurement probe according to the first modification of the second embodiment of the present invention viewed from a side of a distal end of the measurement probe.

Next, a first modification of the second embodiment will be described. FIG. 14 is a cross-sectional diagram of a measurement probe according to a first modification of the second embodiment. FIG. 15 is a front view of the measurement probe according to the first modification of the second embodiment viewed from the side of the distal end of the measurement probe.

A measurement probe 3d illustrated in FIGS. 14 and 15 further includes a plurality of contact detecting fibers 35d to 35i (detection regions d14 to d16) in addition to the elements of the measurement probe 3c according to the second embodiment described above. The contact detecting fibers 35d to 35i are realized by using the optical fibers similarly to the above-mentioned contact detecting fibers 35a to 35c. The contact detecting fibers 35d to 35i detect the return light of the illumination light and propagate the return light to the fourth detection unit 207. Also, the contact detecting fibers 35a to 35i are arranged around the illumination region d1 irradiated by the illuminating fiber 31. Specifically, the contact detecting fibers 35a to 35i are arranged at predetermined intervals in a radial direction of a surface perpendicular to the longitudinal direction along the measurement probe 3d, and for example, three of them are arranged side by side. The contact detecting fibers 35a to 35i are arranged at a predetermined interval (angle), for example, an interval of 120°.

According to the first modification of the second embodiment described above, even when the intensity of the return light has rapidly decreased by dust and foreign substances on one of the distal ends of the measurement probe 3d, the determination unit 211a determines whether the distal end of the measurement probe 3d contacts the measuring target SP1 based on the intensities of the return light detected by all the contact detecting fibers 35a to 35i. Accordingly, the contact with the measuring target SP1 can be accurately determined.

Second Modification of Second Embodiment

Figure 16:
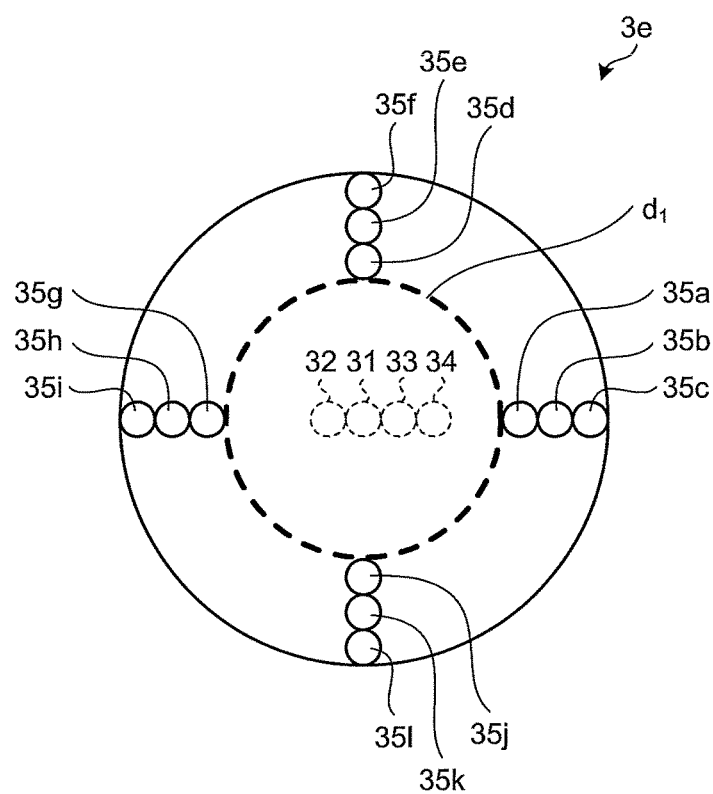
FIG. 16 is a front view of the measurement probe according to a second modification of the second embodiment of the present invention viewed from a side of a distal end of the measurement probe.

Next, a second modification of the second embodiment will be described. FIG. 16 is a front view of a measurement probe according to the second modification of the second embodiment viewed from the side of the distal end of the measurement probe.

A measurement probe 3e illustrated in FIG. 16 further includes a plurality of contact detecting fibers 35d to 35l in addition to the elements of the measurement probe 3c according to the second embodiment described above. The contact detecting fibers 35d to 35l are realized by using the optical fibers similarly to the above-mentioned contact detecting fibers 35a to 35c. The contact detecting fibers 35d to 35l detect the return light of the illumination light and propagate the return light to the fourth detection unit 207. Also, the contact detecting fibers 35a to 35l are arranged side by side by three in a radial direction of the measurement probe 3e and arranged at respective positions which are rotationally symmetric having the center of the measurement probe 3e as an axis. Specifically, the contact detecting fibers 35a to 35l are arranged by three at a predetermined interval, for example, an interval of 90°.

According to the second modification of the second embodiment described above, even when the intensity of the return light has rapidly decreased by dust and foreign substances on one of the distal ends of the measurement probe 3e, the determination unit 211a determines whether the distal end of the measurement probe 3e contacts the measuring target SP1 based on the intensities of the return light detected by all the contact detecting fibers 35a to 35l. Accordingly, the contact with the measuring target SP1 can be accurately determined.

Third Modification of Second Embodiment

Figure 17:
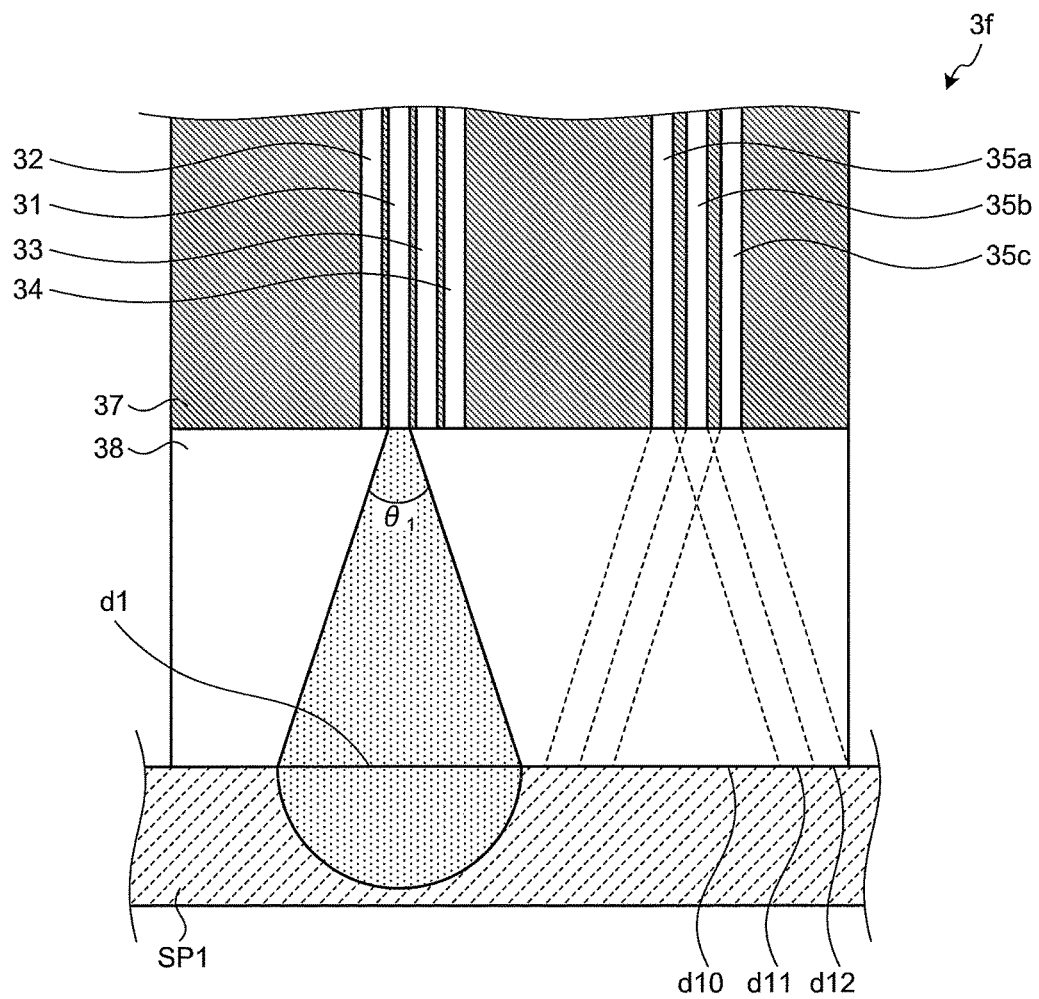
FIG. 17 is a cross-sectional diagram of a measurement probe according to a third modification of the second embodiment of the present invention.

Next, a third modification of the second embodiment will be described. FIG. 17 is a cross-sectional diagram of a measurement probe according to the third modification of the second embodiment.

In a measurement probe 3f illustrated in FIG. 17, the contact detecting fibers 35a to 35c are held by the fiber holding unit 37 in the same lines as each of the first light receiving fiber 32, the second light receiving fiber 33, and the third light receiving fiber 34. In addition, the contact detecting fibers 35a to 35c detect the return light of the illumination light irradiated by the illuminating fiber 31 via the rod lens 38. In addition, the detection regions d10 to d12 of the respective contact detecting fibers 35a to 35c on the distal end face of the measurement probe 3f are held by the fiber holding unit 37 so as to be arranged outside the illumination region d1 irradiated by the illuminating fiber 31 on the distal end face of the measurement probe 3f.

According to the third modification of the second embodiment described above, the measurement probe 3f can be made with a simple structure. In addition, the illuminating fiber 31, the first light receiving fiber 32, the second light receiving fiber 33, the third light receiving fiber 34, and the contact detecting fibers 35a to 35c of the measurement probe 3f can be integrally formed by using a single fiber bundle.

Fourth Modification of Second Embodiment

Figure 18:
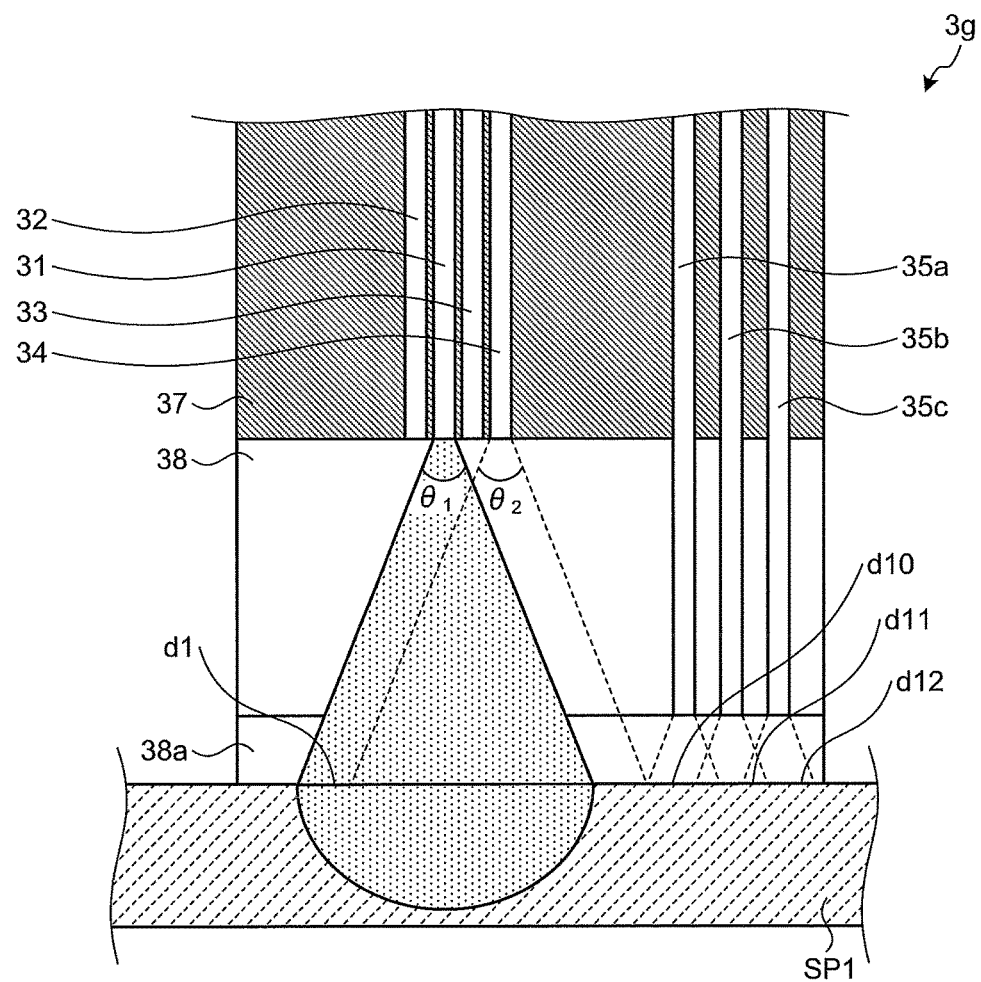
FIG. 18 is a cross-sectional diagram of a measurement probe according to a fourth modification of the second embodiment of the present invention.

Next, a fourth modification of the second embodiment will be described. FIG. 18 is a cross-sectional diagram of a measurement probe according to the fourth modification of the second embodiment.

A measurement probe 3g illustrated in FIG. 18 further includes an optical member 38a for protecting the distal end faces of the contact detecting fibers 35a to 35c and the distal end face of the rod lens 38 in addition to the elements of the measurement probe 3c according to the second embodiment described above.

The optical member 38a (second rod lens) is formed of a similar member to that of the rod lens 38. A glass rod or plastic rod which has light transmission properties and does not have a light pass bending effect as that of the lens, or an optical lens or a refractive index distribution type lens (GRIN lens) having curvature is used for the optical member 38a. The optical member 38a has a disc-like shape and prevents liquid and the like from entering a gap between the contact detecting fibers 35a to 35c and the rod lens 38. The distal end face of the optical member 38a may be obliquely notched relative to the longitudinal direction of the measurement probe 3g. In addition, the optical member 38a may be formed to have no difference between refractive indexes of materials of the rod lens 38 and the optical member 38a so that unnecessary light reflected from the distal end face of the rod lens 38 does not reach the first light receiving fiber 32, the second light receiving fiber 33, and the third light receiving fiber 34 before the illumination light reaches the measuring target SP1 in a bonding part between the rod lens 38 and the optical member 38a. In addition, the rod lens 38 may be obliquely formed relative to the longitudinal direction of the measurement probe 3g similarly to the optical member 38a.

According to the fourth modification of the second embodiment described above, the liquid for entering the gap between the contact detecting fibers 35a to 35c and the rod lens 38 can be surely prevented. Accordingly, when the measurement probe 3g is cleaned or used for the subject, impurities such as water can be surely prevented from entering the above-mentioned gap.

Fifth Modification of Second Embodiment

Figure 19:
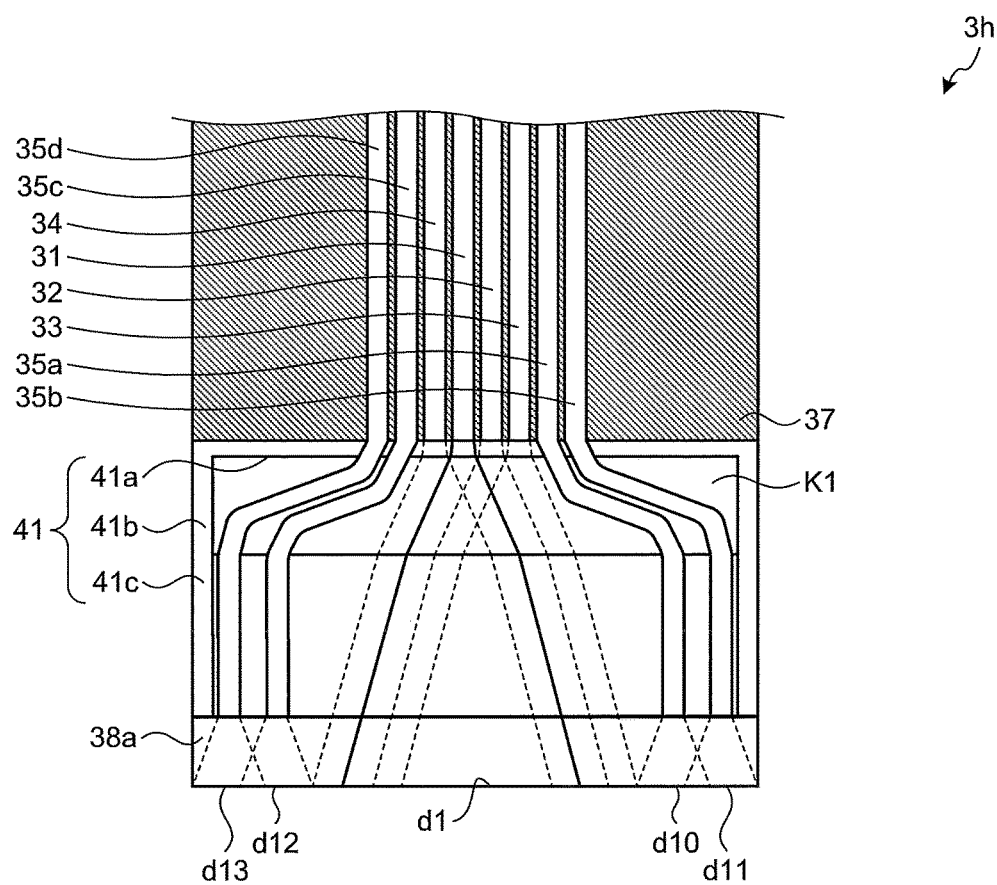
FIG. 19 is a cross-sectional diagram of a measurement probe according to a fifth modification of the second embodiment of the present invention.

Next, a fifth modification of the second embodiment will be described. FIG. 19 is a cross-sectional diagram of a measurement probe according to the fifth modification of the second embodiment.

A measurement probe 3h illustrated in FIG. 19 further includes a contact detecting fiber 35d in addition to the elements of the measurement probe 3c according to the second embodiment described above. In addition, the measurement probe 3h includes a rod lens 41 instead of the rod lens 38 and the optical member 38a according to the fourth modification of the above-mentioned second embodiment.

The rod lens 41 is provided on the distal end of the fiber holding unit 37 and is realized by using glass, plastic, and the like having predetermined permeability. The rod lens 41 has a cylindrical shape so that a distance between each of the distal ends of the illuminating fiber 31, the first light receiving fiber 32, the second light receiving fiber 33, and the third light receiving fiber 34 and the measuring target becomes constant. Also, the rod lens 41 holds the contact detecting fibers 35a to 35d so that the distal ends thereof are exposed. The rod lens 41 includes a disk-shaped bottom 41a, a wall part 41b extending from a circumference of the bottom 41a along the longitudinal direction of the measurement probe 3h, and a cylindrical distal end part 41c. The bottom 41a, the wall part 41b, and the distal end part 41c are integrally formed by bonding with, for example, an adhesive. Accordingly, a space is formed in the rod lens 41. In addition, the optical member 38a is provided on the side of the distal end of the rod lens 41.

According to the fifth modification of the second embodiment described above, the contact detecting fibers 35a to 35d can be easily mounted on the distal end of the rod lens 41 by forming a space K1 in the rod lens 41.

Third Embodiment

Next, a third embodiment of the present invention will be described. A bio-optical measurement system according to the third embodiment has a different configuration from that of the bio-optical measurement system 1 according to the above-mentioned first embodiment. Specifically, the bio-optical measurement system according to the third embodiment further includes a light source unit for irradiating illumination light to detect a contact between a measurement probe and a measuring target and an illuminating fiber. Therefore, the configuration of the bio-optical measurement system according to the third embodiment will be described below. The same reference signs are used to designate the same elements as those of the above-mentioned bio-optical measurement system 1 according to the first embodiment, and the explanation thereof will be omitted.

Configuration of Bio-Optical Measurement System

Figure 20:
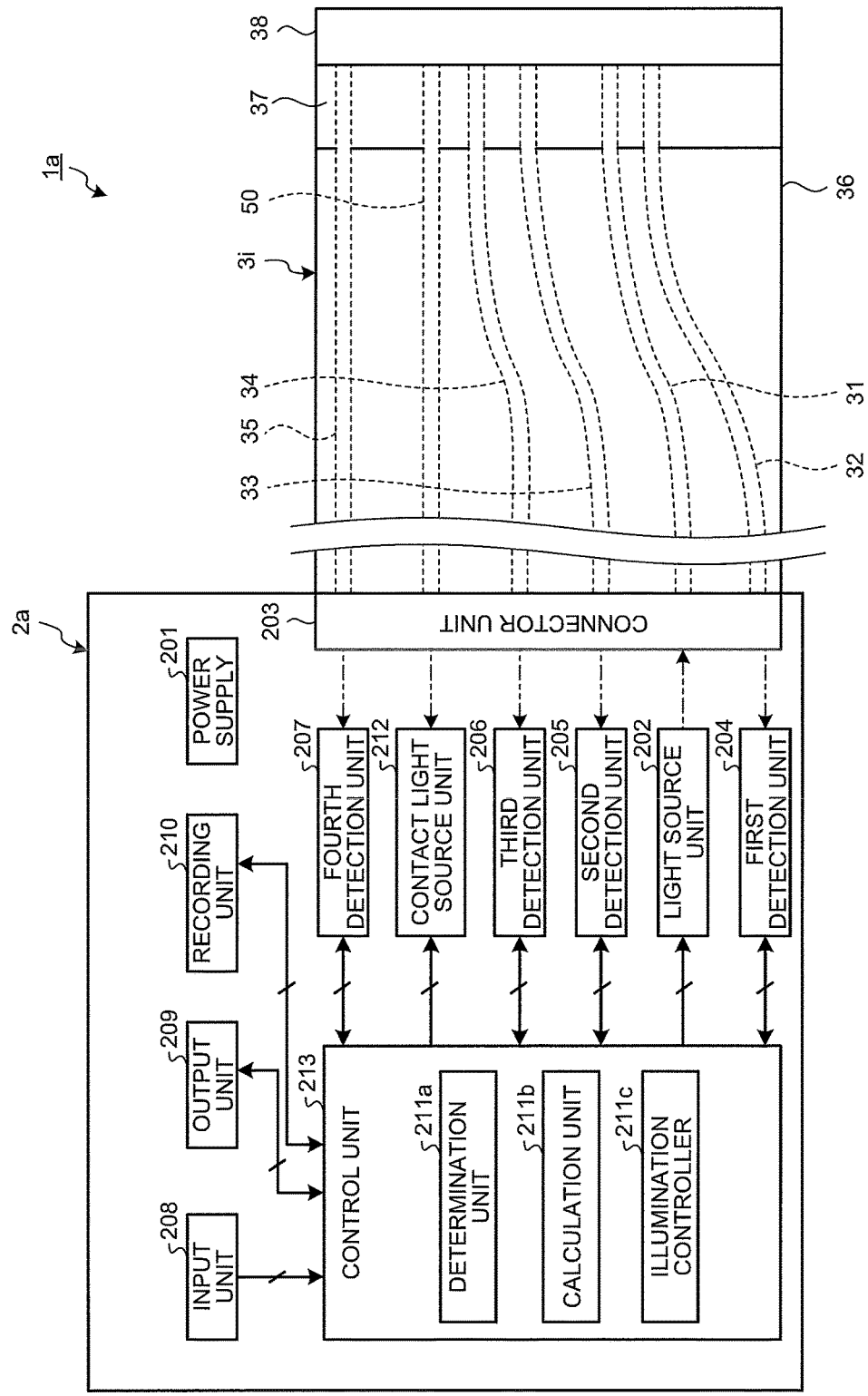
FIG. 20 is a block diagram of a functional configuration of a bio-optical measurement system according to a third embodiment of the present invention.

FIG. 20 is a block diagram of a functional configuration of the bio-optical measurement system according to the third embodiment of the present invention. A bio-optical measurement system 1a illustrated in FIG. 20 includes a bio-optical measurement apparatus 2a for detecting characteristics (property) of the measuring target by performing optical measurement on the measuring target such as body tissues which are scatterers and a measurement probe 3*i* detachably connected to the bio-optical measurement apparatus 2*a*. A side of a distal end of the measurement probe 3*i* is inserted into a subject.

Configuration of Bio-Optical Measurement Apparatus

First, the configuration of the bio-optical measurement apparatus 2*a* will be described. The bio-optical measurement apparatus 2*a* illustrated in FIG. 20 includes a contact light source unit 212 in addition to the elements of the bio-optical measurement apparatus 2 of the first embodiment described above. In addition, the bio-optical measurement apparatus 2*a* includes a control unit 213 instead of the control unit 211 of the bio-optical measurement apparatus 2 of the first embodiment described above.

The contact light source unit 212 irradiates the measuring target such as the body tissues with the illumination light (contact illumination light) via a connector unit 203 and a measurement probe 3*i* under the control of the control unit 213. The contact light source unit 212 is configured of an incoherent light source such as a white LED, a xenon lamp, a tungsten lamp, and a halogen lamp and a coherent light source such as a laser. In addition, the contact light source unit 212 is formed by combining it with an optical lens so that a light guiding efficiency to the optical fiber in the measurement probe 3*i* can be improved.

The control unit 213 totally controls the bio-optical measurement apparatus 2*a* by transferring command information and data to each element of the bio-optical measurement apparatus 2*a*. The control unit 213 is formed by using a CPU and the like. The control unit 213 includes a determination unit 211*a*, a calculation unit 211*b*, and an illumination controller 211*c*.

The illumination controller 211*c* controls the contact light source unit 212 and the light source unit 202 based on the determination result of the determination unit 211*a*. Specifically, when the determination unit 211*a* determines that the distal end of the measurement probe 3*i* does not contact the measuring target, the illumination controller 211*c* causes the contact light source unit 212 to emit the illumination light for detecting the contact. On the other hand, when the determination unit 211*a* determines that the distal end of the measurement probe 3*i* contacts the measuring target, the determination unit 211*a* stops the illumination light for detecting the contact irradiated by the contact light source unit 212 and causes the light source unit 202 to emit the illumination light.

Configuration of Measurement Probe

Figure 21:
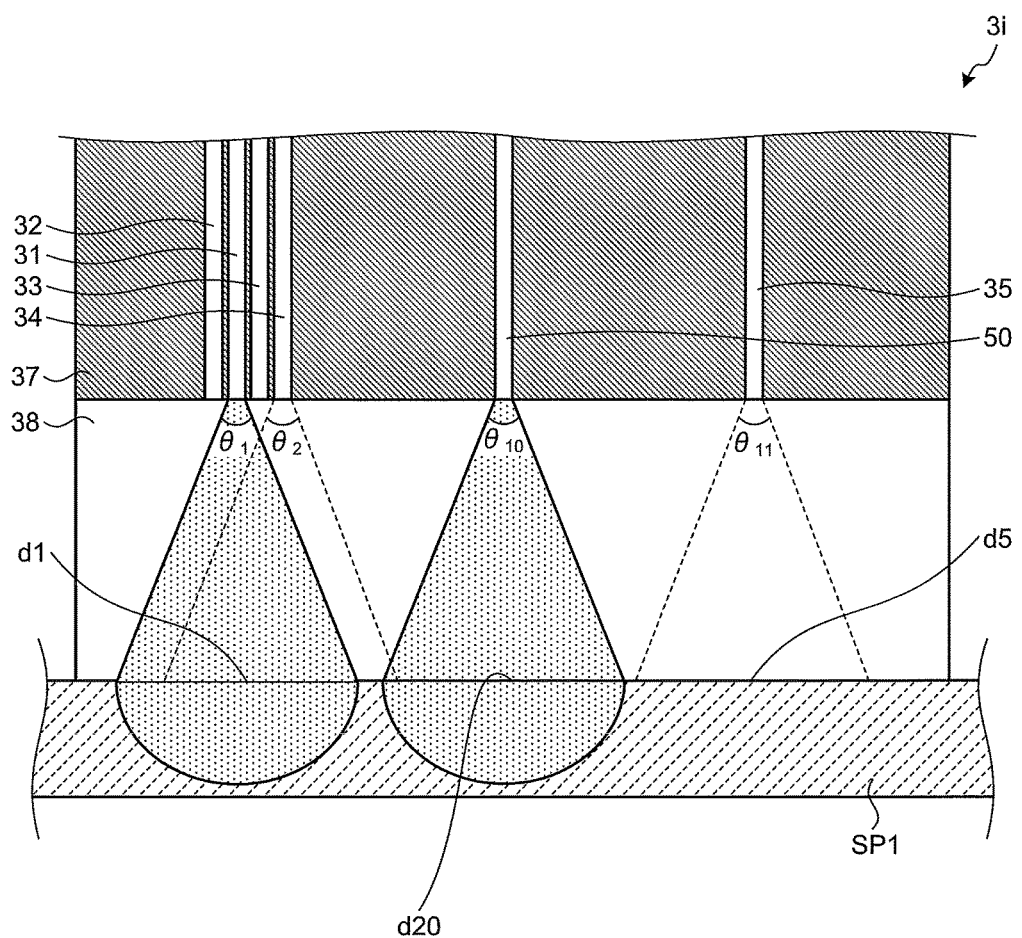
FIG. 21 is a cross-sectional diagram of a measurement probe according to the third embodiment of the present invention.

Next, the configuration of the measurement probe 3*i* will be described. A case will be described below where the number of detecting fibers is three. However, the same can be applied to a case where there is a plurality of detecting fibers in addition to the three detecting fibers. FIG. 21 is a cross-sectional diagram of the measurement probe 3*i*.

The measurement probe 3*i* illustrated in FIG. 21 further includes a contact illuminating fiber 50 in addition to the elements of the measurement probe 3 according to the first embodiment described above. The contact illuminating fiber 50 propagates the illumination light irradiated by the contact light source unit 212 and emits the illumination light from the distal end of the measurement probe 3*i*. An illumination region d20 (contact illumination region) on the distal end face of the measurement probe 3*i* irradiated by the contact illuminating fiber 50 is held by the fiber holding unit 37 so as to be arranged outside the illumination region d1 irradiated by the illuminating fiber 31.

The bio-optical measurement system 1*a* formed in this way is used by using the endoscope system 100 illustrated in FIG. 5 similarly to the above-mentioned first embodiment.

Processing of Bio-Optical Measurement System

Figure 22:
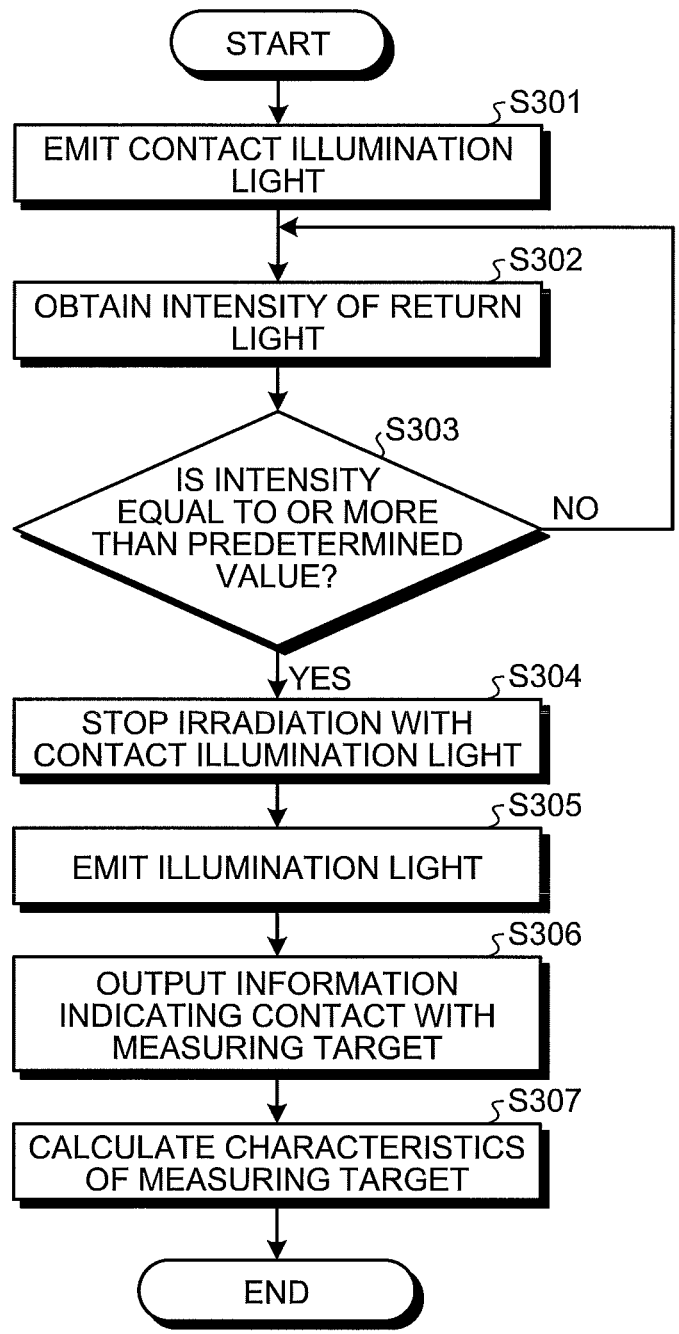
FIG. 22 is a flowchart of an outline of processing performed by the bio-optical measurement system according to the third embodiment of the present invention.

Next, processing performed by the above-mentioned bio-optical measurement system 1*a* will be described. FIG. 22 is a flowchart of an outline of the processing performed by the bio-optical measurement system 1*a*.

As illustrated in FIG. 22, first, the illumination controller 211*c* causes the contact light source unit 212 to emit the contact illumination light (step S301).

Steps S302 and S303 respectively correspond to the above-mentioned steps S101 and S102 in FIG. 6.

Subsequently, the illumination controller 211*c* stops irradiation of the contact illumination light by the contact light source unit 212 (step S304) and causes the light source unit 202 to emit the illumination light (step S305).

Steps S306 and S307 respectively correspond to the above-mentioned steps S103 and S104 in FIG. 6.

According to the third embodiment described above, the contact illuminating fiber 50 for emitting the illumination light to detect whether the distal end of the measurement probe 3*i* contacts the measuring target SP1 is provided in addition to the illuminating fiber 31. Accordingly, the contact with the measuring target SP1 can be detected without being limited by the numerical aperture of the illuminating fiber 31.

Also, according to the third embodiment, the illumination controller 211*c* controls the irradiations by the contact light source unit 212 and the light source unit 202 based on the determination result by the determination unit 211*a*. Therefore, the contact with the measuring target SP1 can be detected without having an effect of the other illumination light, and the characteristics of the measuring target SP1 can be obtained.

There is one contact detecting fiber 35 in the third embodiment. However, a plurality of contact detecting fibers may be employed.

In addition, in the third embodiment, the above-mentioned optical member 38*a* of the fourth modification of the second embodiment may be provided at the distal end of the rod lens 38.

First Modification of Third Embodiment

Figure 23:
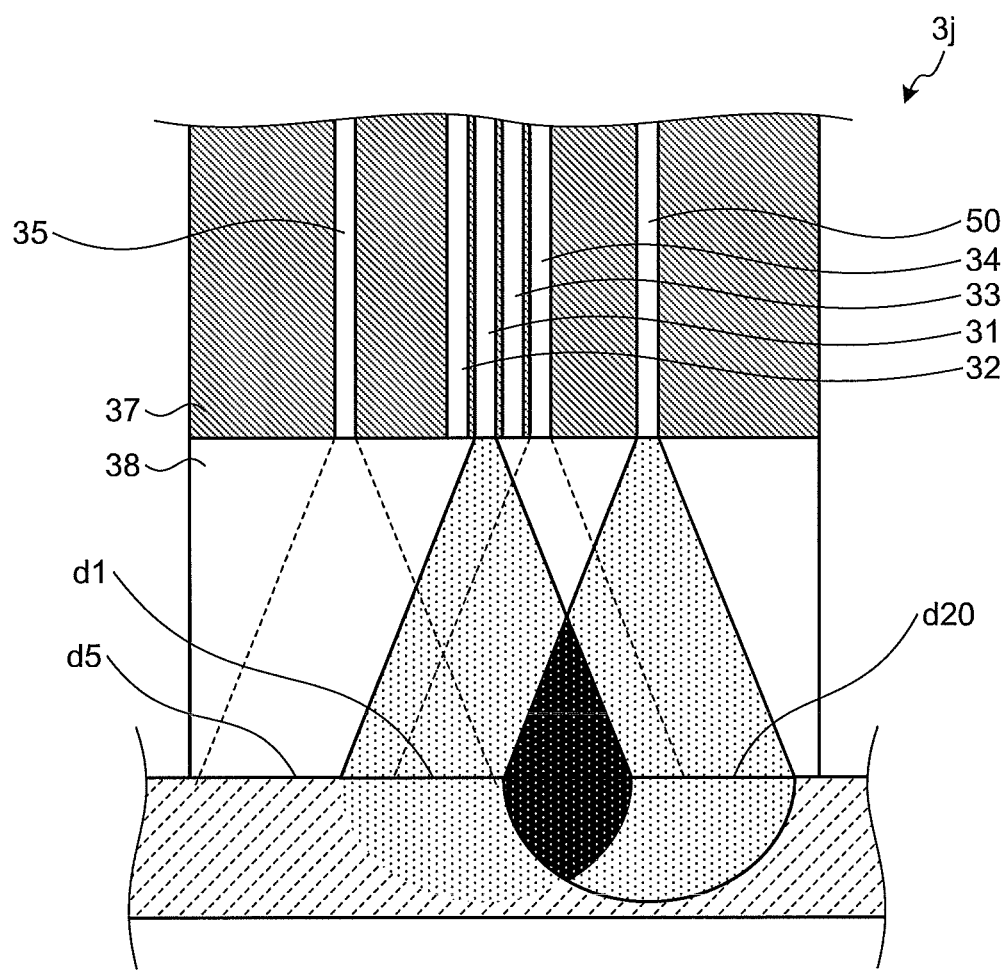
FIG. 23 is a cross-sectional diagram of a measurement probe according to a first modification of the third embodiment of the present invention.

Next, a first modification of the third embodiment will be described. FIG. 23 is a cross-sectional diagram of a measurement probe 3*j* according to the first modification of the third embodiment.

The measurement probe 3*j* illustrated in FIG. 23 has similar elements to those of the above-mentioned measurement probe 3*i* according to the third embodiment. The measurement probe 3*j* is held by the fiber holding unit 37 and arranged such that the illumination region d20 of the contact illuminating fiber 50 on the distal end face of the measurement probe 3*j* overlaps with a part of the illumination region d1 irradiated by the illuminating fiber 31. In addition, the measurement probe 3*j* is held by the fiber holding unit 37 and arranged such that the illumination region d20 of the contact illuminating fiber 50 on the distal end face of the measurement probe 3*j* does not overlap with the detection region d5 of the contact detecting fiber 35.

According to the first modification of the third embodiment described above, the measurement probe 3*j* is held by the fiber holding unit 37 and arranged such that the illumination region (irradiation region) of the contact illuminating fiber 50 on the distal end face of the measurement probe 3j overlaps with a part of the illumination region irradiated by the illuminating fiber 31. Accordingly, it is possible to reduce the diameter of the measurement probe 3j.

Second Modification of Third Embodiment

Figure 24:
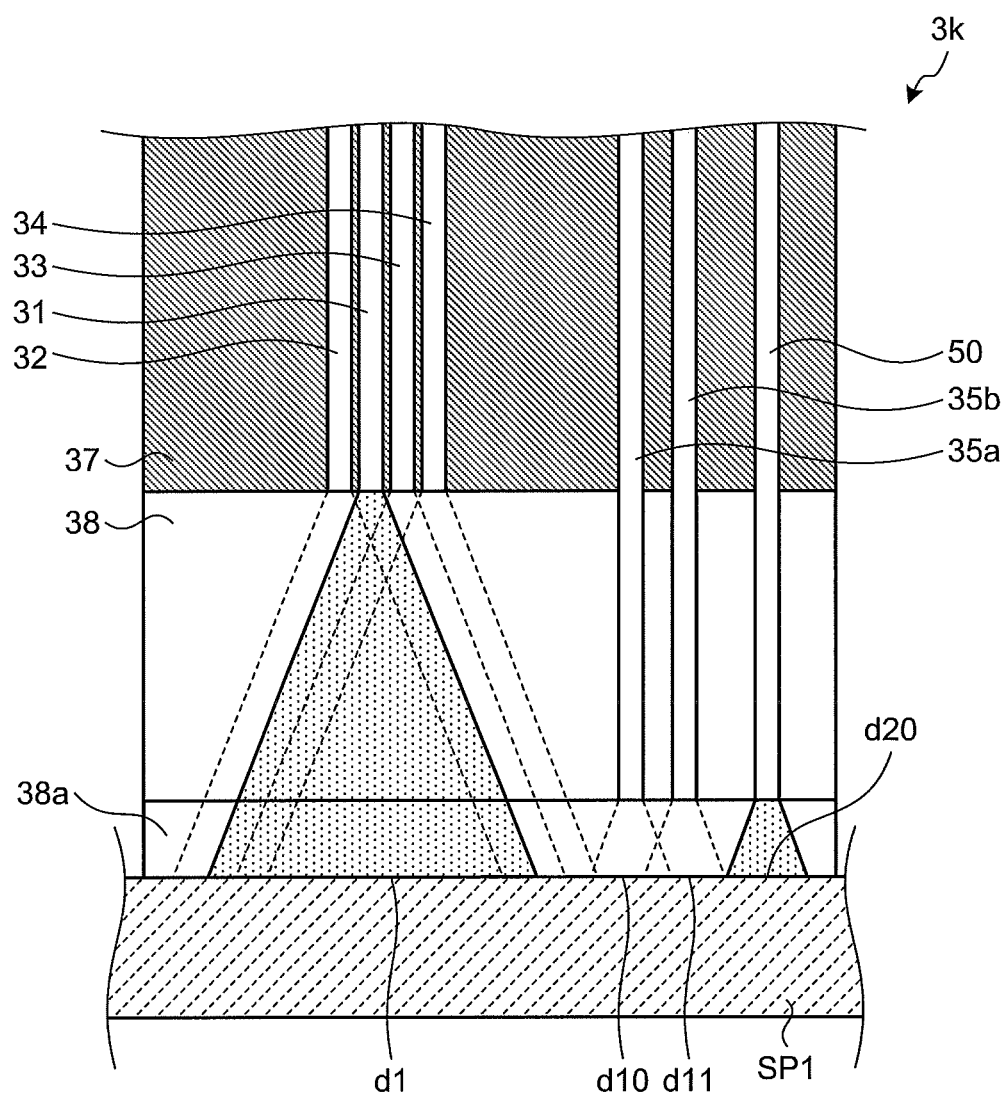
FIG. 24 is a cross-sectional diagram of a measurement probe according to a second modification of the third embodiment of the present invention.
Figure 25:
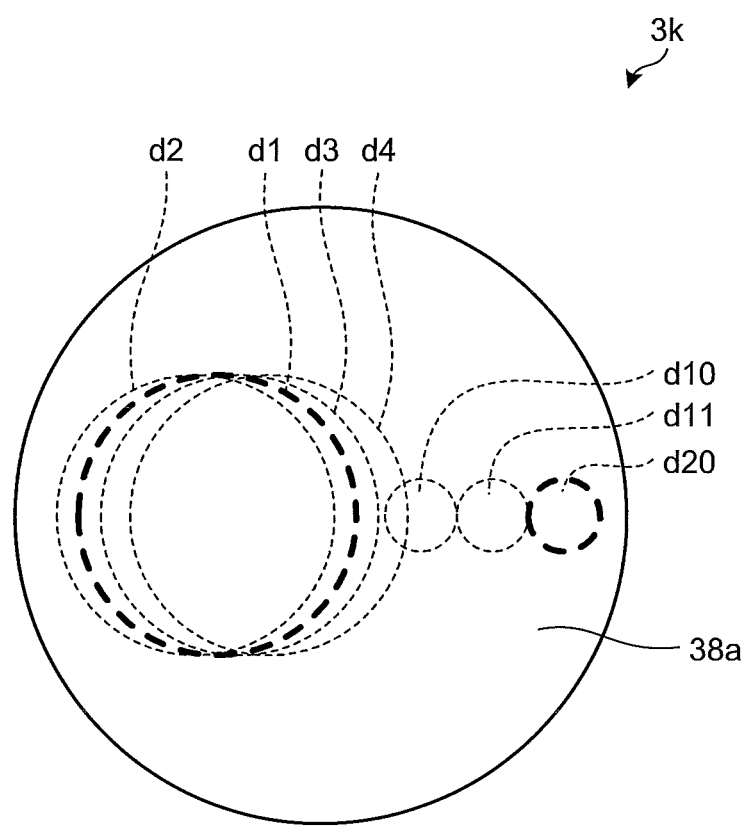
FIG. 25 is a front view of the measurement probe according to the second modification of the third embodiment of the present invention viewed from a side of a distal end of the measurement probe.

Next, a second modification of the third embodiment will be described. FIG. 24 is a cross-sectional diagram of a measurement probe 3k according to the second modification of the third embodiment. FIG. 25 is a front view of the measurement probe 3k according to the second modification of the third embodiment viewed from a side of the distal end.

The measurement probe 3k illustrated in FIGS. 24 and 25 has similar elements to those of the above-mentioned measurement probe 3i of the third embodiment and includes contact detecting fibers 35a and 35b and a contact illuminating fiber 50. The measurement probe 3k is held by the fiber holding unit 37 and arranged such that the illumination region d20 of the contact illuminating fiber 50 on the distal end face of the measurement probe 3k does not overlap with the illumination region d1 irradiated by the illuminating fiber 31. Also, the measurement probe 3k is held by the fiber holding unit 37 and arranged such that the detection regions d10 and d11 of the respective contact detecting fibers 35a and 35b on the distal end face of the measurement probe 3k do not respectively overlap with the illumination region d20 of the contact illuminating fiber 50 and the illumination region d1 irradiated by the illuminating fiber 31.

According to the second modification of the third embodiment described above, the contact illuminating fiber 50 for emitting the illumination light to detect whether the distal end of the measurement probe 3k contacts the measuring target SP1 is provided in addition to the illuminating fiber 31. Accordingly, the contact with the measuring target SP1 can be detected without being limited by the numerical aperture of the illuminating fiber 31.

Third Modification of Third Embodiment

Figure 26:
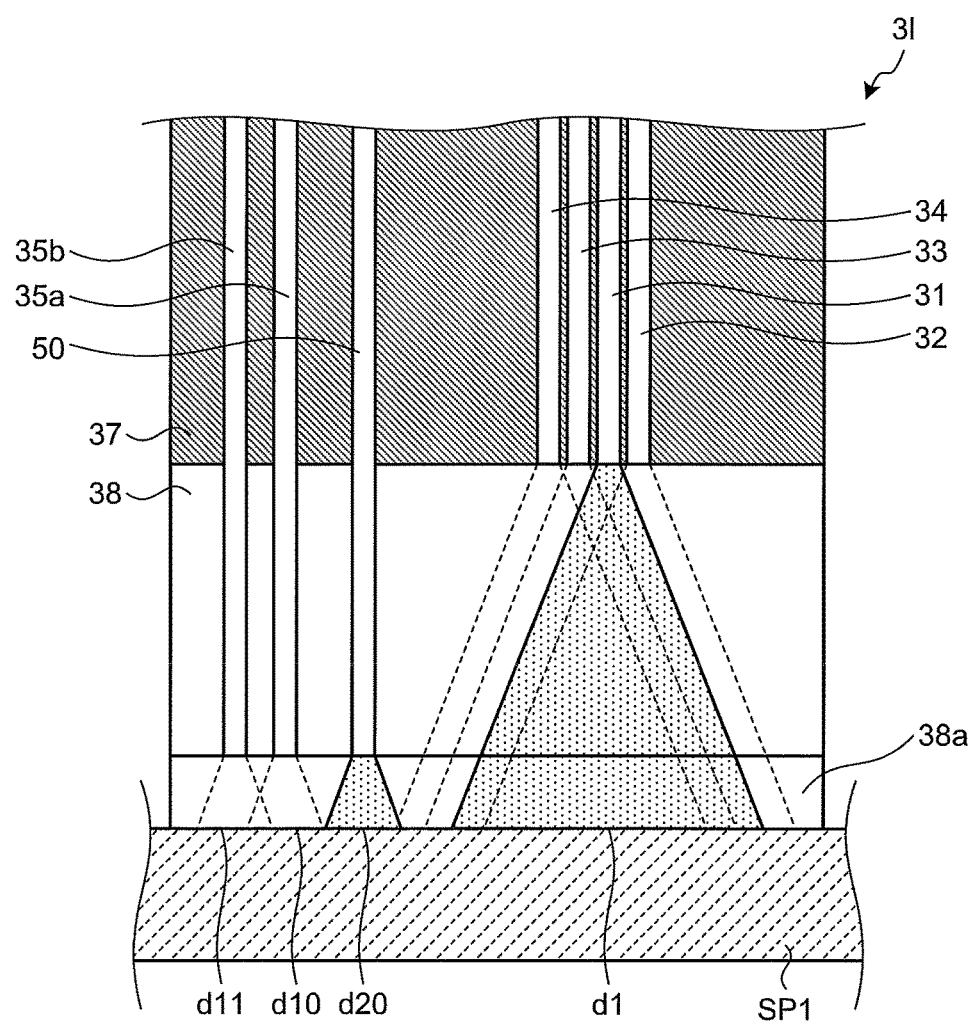
FIG. 26 is a cross-sectional diagram of a measurement probe according to a third modification of the third embodiment of the present invention.
Figure 27:
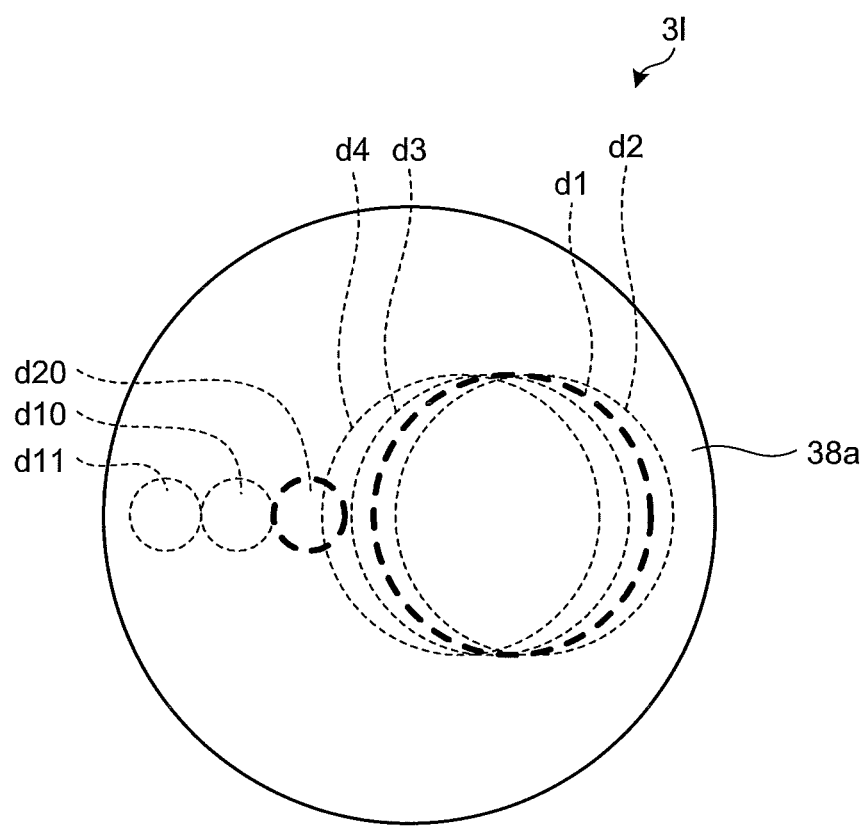
FIG. 27 is a front view of the measurement probe according to the third modification of the third embodiment of the present invention viewed from a side of a distal end of the measurement probe.

Next, a third modification of the third embodiment will be described. FIG. 26 is a cross-sectional diagram of a measurement probe according to the third modification of the third embodiment. FIG. 27 is a front view of the measurement probe according to the third modification of the third embodiment viewed from the side of the distal end.

A measurement probe 31 illustrated in FIGS. 26 and 27 has similar elements to those of the measurement probe 3i according to the third embodiment described above and includes the contact detecting fibers 35a and 35b and the contact illuminating fiber 50. The measurement probe 31 is held by the fiber holding unit 37 and arranged such that the illumination region d20 of the contact illuminating fiber 50 on the distal end face of the measurement probe 31 does not overlap with the illumination region d1 irradiated by the illuminating fiber 31. Also, the measurement probe 31 is held by the fiber holding unit 37 and arranged such that the detection regions d10 and d11 of the respective contact detecting fibers 35a and 35b on the distal end face of the measurement probe 31 do not respectively overlap with the illumination region d20 of the contact illuminating fiber 50 and the illumination region d1 irradiated by the illuminating fiber 31.

According to the third modification of the third embodiment described above, the contact illuminating fiber 50 for emitting the illumination light to detect whether the distal end of the measurement probe 31 contacts the measuring target SP1 is provided in addition to the illuminating fiber 31. Accordingly, the contact with the measuring target SP1 can be detected without being limited by the numerical aperture of the illuminating fiber 31.

In the description of the flowchart herein, the anteroposterior relation of the processing of each step has been defined by using expressions such as "first", "after that", and "subsequently". However, an order of the necessary processing to carry out the present invention is not uniquely defined by those expressions. That is, the order of the processing in the flowchart described herein can be changed within a consistent range.

According to some embodiments, it is possible to determine whether a distal end face surely contacts body tissues.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A measurement probe configured to be detachably connected to a bio-optical measurement apparatus for performing optical measurement on body tissues, the measurement probe comprising:
    an illuminating fiber configured to irradiate the body tissues with illumination light;
    a plurality of light receiving fibers configured to receive return light of at least one of the illumination light reflected and scattered from the body tissues and the illumination light reflected or scattered from the body tissues for measuring a characteristic of the body tissues:
    an optical element configured to transmit the illumination light and the return light and to keep distances between the body tissues and distal ends of the illuminating fiber and the plurality of light receiving fibers constant; and
    a contact detecting fiber configured to receive the return light to detect contact between a distal end face of the optical element and the body tissues, and configured to detect the return light at a detection region on the distal end face through which the illumination light and the return light pass, the detection region being located outside an illumination region of the illuminating fiber; wherein:
    the optical element is a solid element; and
    the contact detecting fiber is embedded in the optical element.

2. The measurement probe according to claim 1, wherein a distance between a position of a distal end of the contact detecting fiber projected perpendicularly on the distal end face and a position of a distal end of the illuminating fiber projected perpendicularly on the distal end face in a direction along the distal end face is longer than a distance between a position of a distal end of each of the plurality of light receiving fibers projected perpendicularly on the distal end face and the position of the distal end of the illuminating fiber projected perpendicularly on the distal end face.

3. The measurement probe according to claim 1, wherein a distance between a distal end of the contact detecting fiber and the distal end face is shorter than a distance between a distal end of each of the plurality of light receiving fibers and the distal end face.

4. The measurement probe according to claim 1, wherein a distance between a distal end of the contact detecting fiber and the distal end face is equal to a distance between a distal end of each of the plurality of light receiving fibers and the distal end face.

5. The measurement probe according to claim 1, further comprising a contact illuminating fiber configured to emit contact illumination light to detect contact between the distal end face and the body tissues, a contact illumination region of the contact illumination light being located outside the illumination region of the illuminating fiber on the distal end face, wherein
the contact detecting fiber is configured to detect the contact using return light of the contact illumination light, and
the detection region of the contact detecting fiber is located outside the contact illumination region on the distal end face.

6. The measurement probe according to claim 1, wherein the contact detecting fiber and one or more additional contact detecting fibers are arranged around the illumination region.

7. The measurement probe according to claim 6, wherein the contact detecting fiber and the one or more additional contact detecting fibers are arranged at predetermined intervals in a radial direction on a plane perpendicular to a longitudinal direction along the measurement probe.

8. The measurement probe according to claim 6, wherein the contact detecting fiber and the one or more additional contact detecting fibers are arranged rotationally symmetric about a central axis of the measurement probe.

9. A bio-optical measurement system comprising:
a bio-optical measurement apparatus configured to perform optical measurement on body tissues; and
a measurement probe configured to be detachably connected to the bio-optical measurement apparatus, wherein
the measurement probe comprises:
an illuminating fiber configured to irradiate the body tissues with illumination light;
a plurality of light receiving fibers configured to receive return light of at least one of the illumination light reflected and scattered from the body tissues and the illumination light reflected or scattered from the body tissues for measuring a characteristic of the body tissues;
an optical element configured to transmit the illumination light and the return light and to keep distances between the body tissues and distal ends of the illuminating fiber and the plurality of light receiving fibers constant; and
a contact detecting fiber configured to receive the return light to detect contact between a distal end face of the optical element and the body tissues, and configured to detect the return light at a detection region on the distal end face through which the illumination light and the return light pass, the detection region being located outside an illumination region of the illuminating fiber,
the bio-optical measurement apparatus comprises:
a detection unit configured to detect an intensity of the return light received by the contact detecting fiber; and
a determination unit configured to determine that the distal end face has contacted the body tissues if decrease in the intensity of the return light detected by the detection unit is equal to or more than a predetermined threshold,
the optical element is a solid element, and
the contact detecting fiber is embedded in the optical element.

10. The bio-optical measurement system according to claim 9, wherein
the measurement probe further comprises a contact illuminating fiber configured to emit contact illumination light to detect contact between the distal end face and the body tissues, a contact illumination region of the contact illumination light being located outside the illumination region of the illuminating fiber on the distal end face,
the contact detecting fiber is configured to detect the contact using return light of the contact illumination light,
the detection region of the contact detecting fiber is located outside the contact illumination region on the distal end face, and
the bio-optical measurement apparatus further comprises:
a light source unit configured to irradiate the illuminating fiber with the illumination light;
a contact light source unit configured to irradiate the contact illuminating fiber with the contact illumination light; and
an illumination controller configured to stop the contact illumination light irradiated by the contact light source unit and to cause the light source unit to emit the illumination light when the determination unit determines that the distal end face has contacted the body tissues.

11. The bio-optical measurement system according to claim 9, wherein
the contact detecting fiber and one or more additional contact detecting fibers are arranged around the illumination region, and
the determination unit is configured to determine that the distal end face has contacted the body tissues when the decrease in the intensity of the return light detected by the detection unit via each of the contact detecting fiber and one or more additional contact detecting fibers is equal to or more than a predetermined threshold.

* * * * *

UNITED STATES PATENT AND TRADEMARK OFFICE
CERTIFICATE OF CORRECTION

PATENT NO. : 10,682,043 B2
APPLICATION NO. : 15/499512
DATED : June 16, 2020
INVENTOR(S) : Koji Matsumoto It is certified that error appears in the above-identified patent and that said Letters Patent is hereby corrected as shown below:

On the Title Page

Item (54) and in the Specification Column 1, Line 1, replace the title as follows:
MEASUREMENT PROBE AND BIO-OPTICAL MEASUREMENT SYSTEM Signed and Sealed this
Eighteenth Day of August, 2020

Andrei Iancu
*Director of the United States Patent and Trademark Office*